(12) United States Patent
El Sabahy et al.

(10) Patent No.: US 11,654,114 B2
(45) Date of Patent: May 23, 2023

(54) ORAL PROLONGED DRUG DELIVERY PLATFORMS

(71) Applicant: Egy-Nano Pharma, LP, Assiut (EG)

(72) Inventors: Mahmoud Fahmy Ali El Sabahy, College Station, TX (US); Mostafa Ahmad Mostafa Mohammad Hamad, Assiut (EG)

(73) Assignee: EGY-NANO PHARMA, LP, Assiut (EG)

( * ) Notice: Subject to any disclaimer, the term of this patent is extended or adjusted under 35 U.S.C. 154(b) by 0 days.

(21) Appl. No.: 16/615,322

(22) PCT Filed: May 18, 2018

(86) PCT No.: PCT/US2018/033462
§ 371 (c)(1),
(2) Date: Nov. 20, 2019

(87) PCT Pub. No.: WO2018/226383
PCT Pub. Date: Dec. 13, 2018

(65) Prior Publication Data
US 2020/0163894 A1    May 28, 2020

Related U.S. Application Data

(60) Provisional application No. 62/516,557, filed on Jun. 7, 2017.

(51) Int. Cl.
| | |
|---|---|
| *A61K 9/00* | (2006.01) |
| *A61K 9/20* | (2006.01) |
| *A61K 9/24* | (2006.01) |
| *A61P 3/10* | (2006.01) |
| *A61K 9/48* | (2006.01) |
| *A61K 38/28* | (2006.01) |

(52) U.S. Cl.
CPC .......... *A61K 9/4866* (2013.01); *A61K 9/0034* (2013.01); *A61K 9/4858* (2013.01); *A61K 38/28* (2013.01)

(58) Field of Classification Search
CPC .. A61K 9/0053; A61K 9/4891; A61K 31/715; A61K 9/1652; A61K 9/50; A61K 9/5036; A61K 9/2086; A61K 2039/542; A61K 9/006; A61K 47/36; A61K 9/20; A61K 9/209; A61K 2300/00; A61K 38/28; A61K 48/0075; A61K 48/005; A61K 9/0209; A61K 9/005; A61K 9/286; A61K 39/542; A61L 29/16; A61L 2300/62; A61P 3/10
See application file for complete search history.

(56) References Cited

U.S. PATENT DOCUMENTS

| | | | | |
|---|---|---|---|---|
| 4,713,243 A | * | 12/1987 | Schiraldi | A61P 25/02 424/676 |
| 5,484,610 A | * | 1/1996 | Bae | A61K 9/1635 424/487 |
| 5,800,832 A | | 9/1998 | Tapolsky et al. | |
| 6,018,033 A | | 1/2000 | Chen et al. | |
| 6,692,766 B1 | * | 2/2004 | Rubinstein | A61K 9/2013 424/487 |
| 6,818,018 B1 | | 11/2004 | Sawhney | |
| 7,919,072 B1 | | 4/2011 | Sung et al. | |
| 9,205,049 B2 | | 12/2015 | Reddy et al. | |
| 2001/0024658 A1 | * | 9/2001 | Chen | A61P 29/00 424/452 |
| 2007/0238707 A1 | * | 10/2007 | Leonard | A61P 29/00 514/89 |
| 2007/0292506 A1 | * | 12/2007 | Goldenberg | A61K 38/08 424/468 |
| 2008/0241251 A1 | * | 10/2008 | Basit | B01J 13/02 424/489 |
| 2009/0047517 A1 | * | 2/2009 | Caruso | B05D 1/36 427/213.33 |
| 2010/0233253 A1 | * | 9/2010 | Kavimandan | A61K 9/2853 424/451 |
| 2013/0337022 A1 | * | 12/2013 | Pillay | A61K 9/006 424/400 |

FOREIGN PATENT DOCUMENTS

| | | | |
|---|---|---|---|
| CN | 105010934 A | | 11/2015 |
| KR | 100794264 B1 | * | 1/2008 |

OTHER PUBLICATIONS

International Search Report and Written Opinion for Application No. PCT/US2018/033462 dated Aug. 10, 2018.
Extended European Search Report dated Feb. 19, 2021 for Application No. 18812871.4.
Proteaseinhibitoren (Wikipedia); https://de.wikipedia.org/wiki/proteaseinhibitoren.

* cited by examiner

*Primary Examiner* — Tracy Liu
(74) *Attorney, Agent, or Firm* — Patterson + Sheridan, LLP

(57) ABSTRACT

In an embodiment, a pH-responsive drug delivery composition for prolonged drug delivery to a mucosal surface is provided. At acidic pH, the matrix self-seal and forms entity that protects the peptide/drug inside. Upon contact with fluids at neutral pH, the platform forms swollen gel-like matrix that can protect their cargoes, opens and adheres to mucosal surfaces and release their cargoes over extended period of time (e.g., up to one week). In some embodiments, the composition includes a polymer matrix comprising two or more layers and/or polymers, an agent, and one or more of a protease inhibitor and an absorption enhancer; and an enteric coating or capsule encapsulating the polymeric matrix. Methods of making and using the drug delivery platforms are also provided.

14 Claims, 9 Drawing Sheets

ORAL PROLONGED DRUG DELIVERY PLATFORMS

CROSS REFERENCE TO RELATED APPLICATIONS

This application claims benefit to International Application No. PCT/US2018/033462, filed May 18, 2018, the entirety of which is herein incorporated by reference, which claims benefit of U.S. Provisional Patent Application No. 62/516,557 filed Jun. 7, 2017 the entirety of which is herein incorporated by reference.

FIELD

The present disclosure is generally in the field of oral drug delivery platforms providing prolonged release of the drugs following oral administration.

BACKGROUND

Most drug delivery systems are designed to maximize therapeutic efficacy, extend drug release time and stability, increase bioavailability of the drugs, minimize side effects, and improve patient compliance by reducing the dosage frequency. The drug delivery systems may manage the rate of drug release chemically and/or physically, and are broadly categorized into sustained and responsive drug delivery system.

Drugs can be loaded into gels, polymeric micelles, or reservoirs in implant devices. They may be released orally from capsules or tablets, or topically from transdermal patches or ointments or creams. Most conventional dosages are tablets/capsules or solutions for injection. These may exhibit drawbacks such as low concentrations and biodistribution due to poor solubility, rapid breakdown of the drug in vivo, and/or pain or tissue damage on extravasation. Some drugs quickly lose their activity, show cytotoxicity, and lead to tissue damage in addition to unwanted side effects (Sharma et al., *J. Mater. Chem. B*, 1:3410-3418 (2013)). This leads to complications when controlling or treating chronic conditions, such as diabetes mellitus.

Diabetes mellitus is a chronic metabolic disorder characterized by hyperglycemia which is caused by absolute or relative deficiency of insulin. There are two main types of diabetes mellitus. Type I diabetes (juvenile diabetes) is a T-cell mediated autoimmune disease involving destruction of β-cells in pancreatic islet which leads to the body's failure to produce enough insulin. Type II diabetes is a combination of insufficient insulin, which is produced from the pancreas, and a resistance to the action of insulin on the liver and muscles.

Insulin hormone was discovered in 1921 in the pancreatic extracts of dogs. Insulin is a peptide hormone secreted by β-cells of islets of Langerhans in pancreas in response to elevation of blood glucose level which stimulate uptake of glucose by muscle, liver and fat. The deficiency of insulin affects carbohydrate, protein and fat metabolism, which eventually leads to many adverse effects, such as, impaired vision, sensor loss, motor weakness, gastrointestinal problems, postural hypotension, ulceration, tachycardia, ischemia, and, in acute cases, may lead to death. Insulin is the only treatment to Type I diabetic patients. It is the last option to treat uncontrolled Type II diabetic patients. It is the only treatment for pregnant females and it is suitable for patients on surgical operations.

Insulin is degraded by the acidic environment in the stomach, and enzymes in the intestine and in the liver by first pass effect, and thus has very low oral bioavailability. Consequently, the most common route of administration of insulin is the subcutaneous route. However, the subcutaneous route has many disadvantages such as being an invasive technique, lack of patient compliance, peripheral hyperinsulinemia, physiological stress from daily injection, cost, inconvenience, risk of infection, hypertrophy and fat deposition at the site of injection.

Effective oral uptake of insulin could provide improved patient compliance and reduce peripheral hyperinsulinemia. However, in addition to the problems in getting bioactive insulin through the gut, there is poor permeability across intestinal epithelium because of its high molecular weight and hydrophilicity.

There remains a need for drug delivery platforms that improve drug bioavailability and provide prolonged bioactivity of a drug following oral administration.

Therefore, it is an object of the present disclosure to provide drug delivery compositions releasing bioactive drugs for a prolonged period of time after a single oral administration.

It is another object of the present disclosure to provide methods of making the oral drug delivery compositions.

It is another object of the present disclosure to provide methods of using the oral drug delivery compositions.

SUMMARY

Drug delivery platforms providing prolonged drug delivery to a mucosal surface, such as the mouth, intestine, rectum or vaginal vault. The drug delivery platforms include a drug-polymer matrix containing at least two polymeric layers and/or polymers, at least one being mucoadhesive. The polymers may be crosslinked mechanically and/or chemically. The drug delivery platform includes protease inhibitors and/or absorption enhancers. The examples demonstrate that a single oral administration to humans is effective to normalize the blood glucose levels for about two to four days, without inducing hypoglycemia. Methods of making and using the drug delivery platforms are also provided.

In an embodiment, a drug delivery composition is provided. The drug delivery composition includes: a polymer matrix comprising: (1) two or more layers, wherein each layer comprises one or more polymers; (2) an agent comprising: one or more of a therapeutic agent, a prophylactic agent, a diagnostic agent, or a neutraceutical agent, at least a portion of the agent entrapped within the layers of the polymer matrix, between the layers of the polymeric matrix, or entrapped within and between the layers of the polymer matrix; and (3) a protease inhibitor, an absorption enhancer, or a combination thereof, in an amount effective to preserve bioactivity of the agent under conditions present in the gastrointestinal tract; and an enteric coating or capsule encapsulating the polymeric matrix.

In another embodiment, a pH-responsive delivery composition that at acidic pH forms a capsule-like matrix via a self-sealing process to protect an agent inside, and at neutral pH the pH-responsive delivery composition forms a swollen gel-like matrix that unrolls and adheres to a mucosal surface and release the agent over an extended period of time (e.g., up to one week) is provided. The pH-responsive delivery composition includes: a polymer matrix comprising: (1) two or more layers, wherein each layer comprises one or more polymers; (2) an agent comprising: one or more of a therapeutic agent, a prophylactic agent, a diagnostic agent, or a neutraceutical agent, at least a portion of the agent entrapped within the layers of the polymer matrix, between the layers of the polymeric matrix, or entrapped within and between the layers of the polymer matrix; and (3) a protease inhibitor, an absorption enhancer, or a combination thereof, in an amount effective to preserve bioactivity of the agent under conditions present in the gastrointestinal tract; and an enteric coating or capsule encapsulating the polymeric matrix.

In another embodiment, a method of making a composition is provided. The method includes: forming a mixture comprising: (i) the agent, (ii) the one or more polymers, and (iii) the protease inhibitor, the absorption enhancer, or a combination thereof; and crosslinking the mixture to form a crosslinked matrix comprising layers, nanofibers, nanoparticles, or a combination thereof.

In another embodiment, a method is provided. The method includes: administering to a subject a composition.

Various polymers can be used, such as polysaccharides, for example, dextrans, celluloses, pectins, alginates, chitosans, sugars and collagen. Various drugs may be used including small molecules (up to 1000-2000 Daltons), nucleic acids, peptides such as insulin, and proteins such as vaccine antigens. The polymers are typically present in the composition in an effective amount to increase the stability and/or enhance and prolong absorption of the drug in the gastrointestinal tract.

The drug delivery compositions may be combined with excipients or coatings to form drug delivery formulations. Drug delivery formulations may be in a form of suspensions, tablets, capsules, gels, suppositories. In some embodiments, the total amount of the drug is between about 1% and 50% of the total weight of the formulation. The compositions and/or polymers may be degradable or non-degradable. The formulations may be oral suspensions to induce a rapid effect in combination with prolonged release. In some embodiments, the formulation is packaged in an excipient such as an enteric coating or a shell. The formulation may also be formed of, or include, mucoadhesive materials that enhance retention within the gastrointestinal tract.

Methods of using the oral drug delivery compositions are also provided. The methods typically include administering the composition orally, but may in some embodiments be administered to another mucosal tissue, such as the mouth, vagina, or rectum. Typically, the oral drug delivery compositions have greater potency, are effective over a longer time, or a combination thereof, when compared to the potency or effectiveness of the same drug in other forms after a single administration.

The examples show that an exemplary therapeutic protein, insulin, when delivered with the drug delivery composition, controlled blood sugar level in animals and humans over a period of days after single administration. The examples show that the oral drug delivery compositions effectively control blood glucose level for a longer time in the tested animals as compared to controls receiving commercially available injectable insulin administered subcutaneously. It is believed this is achieved via more than one mechanism of action. Exemplary mechanisms include bioadhesion of the composition to the gastrointestinal tract, protection of the drug, e.g., insulin, from degradation in the stomach and intestine, sustained release of the drug over prolonged period of time, increased permeability through intestine, and improved bioavailability. Together this provides a better control of the underlying disease or condition, diabetes, than with currently available injectable or oral formulations.

DETAILED DESCRIPTION

Figure 1:
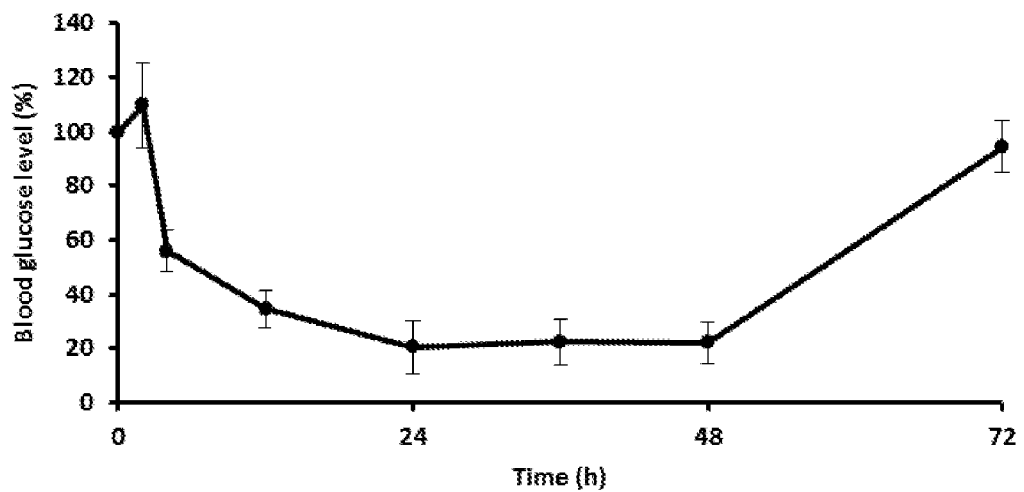
FIG. 1 is a line graph showing the blood glucose level (as percentage of the initial level) over time (h) in a diabetic rabbit following oral administration of the insulin delivery system (100 IU/Kg).

As used herein, the term "prolonged" refers to a period of time that includes at least about two days (about 48 hours), at least about three days (about 72 hours), at least about four days (about 96 hours), at least about five days (about 120 hours), at least about six days (about 144 hours), at least about seven days (about 168 hours), or at least about eight days (about 192 hours) after administration.

As used herein, the terms "active agent" and "drug" refer to a chemical compound that induces a desired pharmacological effect, physiological effect, or both. The terms also encompass pharmaceutically acceptable, pharmacologically active derivatives of those active agents, including, but not limited to, salts, esters, amides, prodrugs, active metabolites, analogs thereof.

As used herein, the term "analog" refers to a given compound, refers to another compound that is structurally similar, functionally similar, or both, to the specified compound. Structural similarity can be determined using any criterion known in the art, such as the Tanimoto coefficient that provides a quantitative measure of similarity between two compounds based on their molecular descriptors. Preferably, the molecular descriptors are 2D properties such as fingerprints, topological indices, and maximum common substructures, or 3D properties such as overall shape, and molecular fields. Tanimoto coefficients range between zero and one, inclusive, for dissimilar and identical pairs of molecules, respectively. A compound can be considered an analog of a specified compound, if it has a Tanimoto coefficient with the compound between 0.5 and 1.0, inclusive, for example between 0.7 and 1.0, inclusive, most for example between 0.85 and 1.0, inclusive. A compound is functionally similar to a specified, if it induces the same pharmacological effect, physiological effect, or both, as the specified compound. "Analog" can also refer to a modification including, but not limited to, hydrolysis, reduction, or oxidation products, of the disclosed compounds. Hydrolysis, reduction, and oxidation reactions are known in the art.

As used herein, the terms "treatment" and "treating" refer to the medical management of a subject with the intent to cure, ameliorate, stabilize, or prevent one or more symptoms of a disease, pathological condition, or disorder. This term includes active treatment, that is, treatment directed specifically toward the improvement of a disease, pathological condition, or disorder, and also includes causal treatment, that is, treatment directed toward removal of the cause of the associated disease, pathological condition, or disorder. In addition, this term includes palliative treatment, that is, treatment designed for the relief of symptoms rather than the curing of the disease, pathological condition, or disorder; preventative treatment, that is, treatment directed to minimizing or partially or completely inhibiting the development of the associated disease, pathological condition, or disorder; and supportive treatment, that is, treatment employed to supplement another specific therapy directed toward the improvement of the associated disease, pathological condition, or disorder.

As used herein the terms "inhibit" and "reduce" refer to reduce or decrease in activity, expression, or level. This can be a complete inhibition or reduction of activity, expression, or level, or a partial inhibition or reduction. Inhibition or reduction can be compared to a control or to a standard level. The inhibition or reduction can be by any increment less than 100% relative to a control. For example, a drug may reduce the level of any one target molecule by about 10%, 15%, 20%, 25%, 30%, 35%, 40%, 45%, 50%, 55%, 60%, 65%, 70%, 75%, 80%, 85%, 90%, 95%, or 99% relative to the level for the same molecule in untreated control cells, tissues, organs, bodies, or subjects that did not receive the drug.

As used herein the terms "increase" and "elevate" refer to an increase in activity, expression, or level. This can be a complete increase of activity, expression, or level, or a partial increase. The increase can be compared to a control or to a standard level. The increase can be by any value, and may be presented in fold increase, percent increase, or as a comparison of numerical values. The increase can be by any increment less than or greater than 100% relative to a control. For example, a drug may increase the level of any one target molecule by about 10%, 15%, 20%, 25%, 30%, 35%, 40%, 45%, 50%, 55%, 60%, 65%, 70%, 75%, 80%, 85%, 90%, 95%, or 99% relative to the level for the same molecule in untreated control cells, tissues, organs, bodies, or subjects that did not receive the drug.

As used herein the terms "effective amount" or "therapeutically effective amount" refer to a dosage sufficient to treat, inhibit, or alleviate one or more symptoms of a disease state being treated or to otherwise provide a desired pharmacologic and/or physiologic effect. The precise dosage will vary according to a variety of factors such as subject-dependent variables (e.g., age, immune system health, etc.), the disease or disorder, and the treatment being administered. The effect of the effective amount can be relative to a control. Such controls are known in the art and discussed herein, and can be, for example, the condition of the subject prior to or in the absence of administration of the drug.

As used herein, the term "combination therapy" refers to treatment of a disease or symptom thereof including administering an effective amount of two or more therapeutic or prophylactic agents to treat one or more symptoms of the disease or symptom thereof, or to produce the physiological change, wherein the agents or components are administered together, such as part of the same composition, or administered separately and independently at the same time or at different times (i.e., administration of each agent or component is separated by a finite period of time from each other).

As used herein, the term "dosage regime" refers to drug formulation, route of administration, dosage, dosing interval and treatment duration.

As used herein, "pharmaceutically acceptable" refers to a material that is can be administered to a subject without causing any undesirable biological effects or interacting in a deleterious manner with any of the other components of the pharmaceutical composition in which it is contained.

As used herein, the term "polypeptides" includes proteins and fragments thereof. Polypeptides are disclosed herein as amino acid residue sequences. As used herein, the term "variant" refers to a polypeptide or polynucleotide that differs from a reference polypeptide or polynucleotide, but retains essential properties. A typical variant of a polypeptide differs in amino acid sequence from another, reference polypeptide. Generally, differences are limited so that the sequences of the reference polypeptide and the variant are closely similar overall and, in many regions, identical. A variant and reference polypeptide may differ in amino acid sequence by one or more modifications (e.g., substitutions, additions, and/or deletions). A substituted or inserted amino acid residue may or may not be one encoded by the genetic code. A variant of a polypeptide may be naturally occurring such as an allelic variant, or it may be a variant that is not known to occur naturally.

Modifications and changes can be made in the structure of the polypeptides of in disclosure and still obtain a molecule having similar characteristics as the polypeptide (e.g., a conservative amino acid substitution). For example, certain amino acids can be substituted for other amino acids in a sequence without appreciable loss of activity. Because it is the interactive capacity and nature of a polypeptide that defines that polypeptide's biological functional activity, certain amino acid sequence substitutions can be made in a polypeptide sequence and nevertheless obtain a polypeptide with like properties.

It is believed that the relative hydropathic character of the amino acid determines the secondary structure of the resultant polypeptide, which in turn defines the interaction of the polypeptide with other molecules, such as enzymes, substrates, receptors, antibodies, and antigens. It is known in the art that an amino acid can be substituted by another amino acid having a similar hydropathic index and still obtain a functionally equivalent polypeptide. In such changes, the substitution of amino acids whose hydropathic indices or hydrophilic values are within ±2 is preferred, those within ±1 are particularly preferred, and those within ±0.5 are even more particularly preferred.

As used herein, the term "hydrophilic" refers to the property of having affinity for water. For example, hydrophilic polymers (or hydrophilic polymer segments) are polymers (or polymer segments) that are primarily soluble in aqueous solutions and/or have a tendency to absorb water. In general, the more hydrophilic a polymer is, the more that polymer tends to dissolve in, mix with, or be wetted by water. Hydrophilicity can be quantified by measuring its partition coefficient between water (or a buffered aqueous solution) and a water-immiscible organic solvent, such as octanol, methylene chloride, or methyl tert-butyl ether. If after equilibration a greater concentration of the compound is attained in water than in the organic solvent, then the compound is considered hydrophilic.

"Identity," as known in the art, is a relationship between two or more polypeptide sequences, as determined by comparing the sequences. In the art, "identity" also means the degree of sequence relatedness between polypeptide as determined by the match between strings of such sequences. "Identity" can also mean the degree of sequence relatedness of a polypeptide compared to the full-length of a reference polypeptide. "Identity" and "similarity" can be readily calculated by known methods, including, but not limited to, those described in (Computational Molecular Biology, Lesk, A. M., Ed., Oxford University Press, New York, 1988; Biocomputing: Informatics and Genome Projects, Smith, D. W., Ed., Academic Press, New York, 1993; Computer Analysis of Sequence Data, Part I, Griffin, A. M, and Griffin, H. G., Eds., Humana Press, New Jersey, 1994; Sequence Analysis in Molecular Biology, von Heinje, G., Academic Press, 1987; and Sequence Analysis Primer, Gribskov, M and Devereux, J., Eds., M Stockton Press, New York, 1991; and CariHo, H., and Lipman, D., SIAM J Applied Math., 48: 1073 (1988).

Various methods to determine identity can be used, such as methods to determine identity that are designed to give the largest match between the sequences tested. Methods to determine identity and similarity are codified in publicly available computer programs. The percent identity between two sequences can be determined by using analysis software (i.e., Sequence Analysis Software Package of the Genetics Computer Group, Madison Wis.) that incorporates the Needelman and Wunsch, (J. Mol. Biol., 48: 443-453, 1970) algorithm (e.g., NBLAST, and XBLAST). The default parameters are used to determine the identity for the polypeptides of the present disclosure.

As used herein, "human insulin" is the human peptide hormone secreted by the pancreas, whether isolated from a natural source or made recombinantly by genetically altered microorganisms. As used herein, "non-human insulin" is the same as human insulin but from an animal source such as pig or cow.

As used herein, an insulin analogue is an altered insulin, different from the insulin secreted by the pancreas, but still available to the body for performing the same action as natural insulin. Through genetic engineering of the underlying DNA, the amino acid sequence of insulin can be changed to alter its ADME (absorption, distribution, metabolism, and excretion) characteristics. Examples include insulin lispro, insulin glargine, insulin aspart, insulin glulisine, and insulin detemir. The insulin can also be modified chemically, for example, by acetylation. As used herein, human insulin analogues are altered human insulin which is able to perform the same action as human insulin.

As used herein, the terms "subject," "individual," and "patient" refer to any individual who is the target of treatment using the disclosed compositions. The subject can be a vertebrate, for example, a mammal. Thus, the subject can be a human. The subjects can be symptomatic or asymptomatic. The term does not denote a particular age or sex. Thus, adult and newborn subjects, whether male or female, are intended to be covered. A subject can include a control subject or a test subject.

As used herein, the term "in need of treatment" refers to a judgment made by a caregiver (e.g. physician, nurse, nurse practitioner, or individual in the case of humans; veterinarian in the case of animals, including non-human mammals) that a subject requires or will benefit from treatment. This judgment is made based on a variety of factors that are in the realm of a care giver's expertise, but that includes the knowledge that the subject is ill, or will be ill, as the result of a condition that is treatable by the compounds of the present disclosure.

As used herein, the term "bioactivity" refers to the effect of the drug on a subject receiving the drug. The effect may be an increase or decrease in a level of a target molecule, or a target organ function, within the subject. For example, a bioactivity of the drug may be a detectable increase or decrease in a level of a target molecule, or a target organ function, observed in the subject receiving the drug when compared to a control.

As used herein, the term "enteral administration" refers to administration via oral or rectal routes. Enteral administration may be oral administration, sublingual administration, gastric administration, or rectal administration.

As used herein, the terms "pharmaceutically acceptable carrier" or "pharmaceutically acceptable excipient" refer to one or more carrier ingredients approved by a regulatory agency of the Federal or a state government or listed in the U.S. Pharmacopoeia or other generally recognized pharmacopoeia for use in animals, mammals, and more particularly in humans.

As used herein, the term "sustained release" refers to release of a substance over an extended period of time in contrast to a bolus type administration in which the entire amount of the substance is made biologically available at one time.

As used herein, the term "biodegradable" generally refers to a material that degrades or breaks down into its component subunits, or digestion, e.g., by a biochemical process, of the material into smaller (e.g., non-polymeric) subunits.

As used herein, "polysaccharide" refers to a compound made from at least two monosaccharide units which are linked via a glycosylic (or glycosidic) bond. Unless otherwise specified, a polysaccharide may contain only sugar components, or may contain non-sugar components as well, such as amino acids and small molecule aglycones. Polysaccharides having a molecular weight (expressed in kDa wherein "Da" stands for "Daltons" and 1 kDa=1,000 Da) greater than about 10,000 Da may be designated "high-molecular-weight polysaccharides," whereas polysaccharides having a molecular weight less than about 10,000 Da may be designated "low-molecular-weight polysaccharides." Polysaccharide molecular weight may be determined using standard methods known to one skilled in the art, including, but not limited to, mass spectrometry (e.g., of digested fragments by ESI or MALDI) or calculation from known carbohydrate sequences. Polysaccharides can be naturally occurring or non-naturally occurring, synthetic, or semi-synthetic.

As used herein, the term "small molecule" refers to molecules with a molecular weight of less than 1000 g/mole, or less than 1000 Dalton (Da).

As used herein, the term "nanofiber" refers to a fiber of material with a thickness or diameter in the range of 1 nm to 2000 nm, while the length may be in the nanometer, micron, or millimeter range or greater.

As used herein, the term "electrospinning" refers to a technique that employs electric forces to elongate and decrease the diameter of a viscoelastic polymer stream, allowing for the formation of solid fibers ranging from nanometers to microns in diameter.

Recitation of ranges of values herein are merely intended to serve as a shorthand method of referring individually to each separate value falling within the range, unless otherwise indicated herein, and each separate value is incorporated into the specification as if it were individually recited herein.

Use of the term "about" is intended to describe values either above or below the stated value in a range of approx. +/−10%; in other embodiments the values may range in value either above or below the stated value in a range of approx. +/−5%; in other embodiments the values may range in value either above or below the stated value in a range of approx. +/−2%; in other embodiments the values may range in value either above or below the stated value in a range of approx. +/−1%. The use of any and all examples, or exemplary language (e.g., "such as") provided herein, is intended merely to better illuminate the present disclosure and does not pose a limitation on the scope of the present disclosure unless otherwise claimed.

I. Drug Delivery Platforms

The drug delivery platforms are polymeric matrix-based compositions and formulations. The compositions typically include a drug-polymer matrix and protease inhibitors and/or absorption enhancers. The compositions release the drug in vivo over a period of several days after a single administration. Bioactivity is measurable for over two days and up to eight days, such as for up to five days, or about four days following a single administration.

The drug delivery compositions may be in a form of formulations. The formulations contain the compositions together with excipients, and/or coatings. The drug delivery compositions may be enclosed in capsule, or coated with an enteric coating for oral, vaginal, or rectal delivery.

Drug bioactivity can be measured in vivo for at least about two days (about 48 hours), at least about three days (about 72 hours), at least about four days (about 96 hours), at least about five days (about 120 hours), at least about six days (about 144 hours), at least about seven days (about 168 hours), or at least about eight days (about 192 hours) following single administration.

A. Drug Delivery Compositions

The drug delivery compositions include a drug-polymer matrix containing one or more therapeutic, prophylactic, diagnostic, or neutraceutical drugs entrapped between two or more polymers. The two or more polymers form a layered or mixed, unlayered matrix, or a combination thereof. Each layer may be formed from one or more polymers. In some embodiments, at least one polymer in the layered or mixed matrix, for example, is in nanofiber form.

The layered matrix is, for example, in the form of a layered matrix entrapping the drug within the layers, between the layers, or both. The layers in the matrix may be crosslinked to each other, the polymers within the layers may be crosslinked to each other, or both the polymers within the layers and between the layers may be crosslinked to each other.

The compositions include a mix of two or more polymers with the one or more drugs in an amount effective to increase the stability of the drug in vivo, prolong the release of the drug in vivo, or a combination thereof.

The interaction between the polymers and the one or more drugs is such that the polymers do not substantially reduce the stability and bioactivity of the drugs when compared to the stability and bioactivity of the drugs in the absence of the polymers. Also, the interaction between the polymers and the one or more drugs is such that the drugs do not substantially reduce the stability of the polymers when compared to the stability of the polymers in the absence of the drug. Substantial reduction may be a reduction by about 10%, about 5%, or about 1%.

Typically, the polymeric matrix includes at least one protease inhibitor.

The polymeric matrix may include one or more absorption enhancer. Generally, the protease inhibitor(s) and/or absorption enhancer(s) are present in an amount effective to provide bioactivity of the drug following single administration For drug delivery formulations, the composition may be folded into a three-dimensional shape. The three-dimensional shape may be coated or mixed with excipients, and may be coated with an enteric coating, and/or enclosed in an acid-resistant capsule, or suppository bases.

1. Polymers

Typically, the polymeric matrix includes at least two polymers. The polymers may be biodegradable or non-biodegradable. The polymers may be synthetic or natural polymers. Generally, at least one of the polymers is a bioadhesive polymer. The polymers may be polysaccharides.

The nature of the polymer, the weight ratio between the different polymers, the form of the polymers, such as cross-linked form, nanofiber form, or a combination of crosslinked and fibrous polymers, and the size of the nanofibers, greatly influence the bioavailability and release of the drug following enteral or vaginal administration of the composition.

Typically, the weight ratio between the two or more polymers is any weight ratio between 1:1 and 1:8, and may be any one of 1:1, 1:1.5, 1:2, 1:2.5, 1:3, 1:3.5, 1:4, 1:4.5, 1:5, 1:5.5, 1:6, 1:6.5, 1:7, 1:7.5, or 1:8, for example from 1:1 to 1.5. Each of the two or more polymers may be present in unmodified form, in crosslinked form, in nanofiber form, or a combination of crosslinked and nanofiber forms.

Exemplary biodegradable polymers include polylactide (PLA), polycaprolactone (PCL), poly(glycolic acid), (PGA), poly(lactidecoglycolide)

(PLGA) random copolymer, poly(D,L-lactide) poly(ethylene glycol) (PLA-PEG) block copolymer, polyimide, poly(ethylene glycol) diacrylate (PEGDA), and poly(ethylene glycol) diacrylamide (PEGDAA); polysaccharides, such as celluloses, alginates, chitosans, hyaluronic acid, glucosaminoglycans, dimethylaminoethyl (DEAE)-cellulose, and DEAE-dextran; hydrophilic poly(amino acids), such as poly-L-glutamic acid, gamma-polyglutamic acid, poly-L-aspartic acid, poly-L-serine, polyornithine, poly-L-arginine, and poly-L-lysine; poly(oxyethylated polyol); poly(olefinic alcohol), such as poly(vinyl alcohol) and aminoacetalized poly(vinyl alcohol); poly(N-vinylpyrrolidone); poly(amidoamine); acrylic or acrylate, and alkacrylic or alkacrylate polymers such as poly(acrylic acid), poly(acrylate), poly(methacrylic acid), poly(methacrylate), poly(hydroxyethyl acrylate); poly(N,N-dimethylaminoethyl methacrylate), poly(N,N-dimethylaminoethyl acrylate), poly(hydroxyalkyl methacrylate) e.g. poly(hydroxyethyl methacrylate); acrylamide polymers such as poly(acrylamide), poly(N,N-dimethylacrylamide), poly(hydroxyalkyl methacrylamide) e.g. poly(hydroxyethyl methacrylamide; poly(ethylene imine); poly(allylamine); poly(vinylamine); and poly(4-vinylpyridine); and copolymers thereof.

a. Polysaccharides

Exemplary biodegradable polymers may include polysaccharides. The polysaccharide may either be naturally occurring or synthetically derived. The polysaccharide may have molecular weights between about 1 and 1,000 kDa, between about 1 and 100 kDa, between about 1 and 50 kDa, between about 1 and 20 kDa, between about 3 and 6 kDa or between about 10 and 20 kDa. In some embodiments, the polysaccharide may have a molecular weight greater than 500 kDa, greater than 750 kDa, or even greater than 1,000 kDa. Certain polysaccharides may have a molecular weight between about 500 and 1,000 kDa, or between about 500 and 750 kDa, or between about 750 and 1,000 kDa.

Polysaccharides may include one or more of the following carbohydrate units: allose, altrose, arabinose, erythrose, erythrulose, fructose, fucitol, fucosamine, fucose, galactosamine, galactosaminitol, galactose, glucosamine, glucosaminitol, glucose, gulose, idose, lyxose, mannosamine, mannose, psicose, quinovose, quinovosamine, rhamnitol, rhamnosamine, rhamnose, ribose, ribulose, sorbose, tagatose, talose, threose, xylose, xylulose, abequose, amicetose, amylose, apiose, arcanose, ascarylose, boivinose, cellobiose, cellotriose, chacotriose, chalcose, cladinose, colitose, cymarose, 2-deoxyribose, 2-deoxyglucose, diginose, digitalose, digitoxose, evalose, evernitrose, gentianose, gentiobiose, hamamelose, inulin, isolevoglucosenone, isomaltose, isomaltotriose, isopanose, kojibiose, lactose, lactosamine, lactosediamine, laminarabiose, levoglucosan, levoglucosenone, maltose, manninotriose, melezitose, melibiose, muramic acid, mycarose, mycinose, neuraminic acid, nigerose, nojirimycin, noviose, oleandrose, panose, paratose, planteose, primeverose, raffinose, rhodinose, rutinose, sarmentose, sedoheptulose, sedoheptulosan, solatriose, sophorose, stachyose, streptose, sucrose, α,α-trehalose, trehalosamine, turanose, tyvelose, umbelliferose, acosamine, bacillosamine, daunosamine, desosamine, forosamine, garosamine, kanosamine, kansosamine, mycaminose, mycosamine, perosamine, pneumosamine, purpurosamine and rhodosamine.

The polysaccharides may be plant- or fungal-derived compounds, including pectins, galactomannans/mannoglycans, xyloglucans, and beta-glucans/lentinans. Other polysaccharides include chitosan, fucoidan, galactan, carrageenan, k-carrageenan, galactofucan, mannoglucoronofucan, arabinogalactans, xylomannan sulfate, xylogalactofucan, ulvan, dextrans and derivatives thereof, and other compounds such as described by Chattopadhyay, *International Journal of Polymer Science,* 2010, 2010:1-7; or Patel, 3 *Biotech,* 2012, 2:171-185).

In some aspects, the polysaccharides may be cellulose, oxidized regenerated cellulose, dextran, pectin, alginate, or chitosan.

For example, when one of the polymers is a chitosan, it may be in a powder form or as nanofibers. Chitosan, either medium—(190,000-310,000 Da, 75-85% deacetylation degree) or high—(310,000-375,000 Da, >75% deacetylation degree) molecular weights, can be used as acetate salts via combining the chitosan with acetic acid.

b. Bioadhesive Polymers

At least one of the polymers in the polymeric matrix may be a bioadhesive polymer. The bioadhesive polymer prolongs the residence time of the drug in the gastrointestinal tract.

Representative bioadhesive polymers include bioerodible hydrogels described by Sawhney, et al., *Macromolecules,* 26:581-87 (1993), as well as polyhyaluronic acids, casein, gelatin, gluten, polyanhydrides, polyacrylic acid, alginate, chitosan, poly(methyl methacrylates), poly(ethyl methacrylates), poly(butylmethacrylate), poly(isobutylmethacrylate), poly(hexlmethacrylate), poly(isodecyl methacrylate), poly(lauryl methacrylate), poly(phenyl methacrylate), poly(methyl acrylate), poly(isopropyl acrylate), poly(isobutyl acrylate), poly(octadecyl acrylate), and poly(fumaric-co-sebacic)acid.

c. Matrix Forms—Crosslinked and Electrospun Polymers

One or more of the polymers in the polymeric matrix may be crosslinked polymers, electrospun polymers, or electrospun crosslinked polymers.

Crosslinking is achieved by physical (non-covalent) intermolecular interactions between the polymer molecules, or by covalently crosslinking the polymer molecules using a suitable initiator (and optionally, activator).

The electrospun polymers are typically nanofibers with a diameter of between several nanometers and several micrometers. The diameter of nanofibers may be between 1 nm and 1000 nm, such as between 5 nm and 800 nm, between 5 nm and 500 nm, between 10 nm and 400 nm, between 10 nm and 200 nm. The length of nanofibers may be several tens of hundreds of nanometers, micrometers, millimeters, or longer.

The polymers of the polymeric matrix may be held together in any suitable interactions. Suitable interactions include physical interaction (intermolecular forces, such as hydrogen bonds, etc.), or chemical crosslinking, such as with the use of chemical initiators or photochemical crosslinking.

The polymeric matrix may be a continuous matrix of two or more interconnected polymers, or layered into two or more layers. Each layer may be a single polymer or two or more interconnected polymers. The drug to be delivered may be entrapped within the polymeric matrices, between the two or more layers, or both within the polymeric matrices and between the two or more layers. For example, each of the polymers in the polymeric matrix may form a polymeric layer, entrapping the drug to be delivered between the polymeric layers. This may form a sandwich-like polymeric matrix, entrapping the drug to be delivered between and/or within two or more layers of crosslinked or network-based polymers. The entrapped drug may be associated with the polymers via covalent bonds, or non-covalent interactions, or both via covalent bonds and non-covalent interactions.

2. Protease Inhibitor

Exemplary protease inhibitors include AEBSF-[4-(2-Aminoethyl) benzenesulfonyl fluoride hydrochloride], aprotinin, bestatin hydrochloride, E-64-[N-(trans-Epoxysuccinyl)-L-leucine 4-guanidinobutylamide], Leupeptin hemisulfate salt, and Pepstatin A.

The protease inhibitors are typically present in the polymer matrix in an amount effective to provide bioactivity of the drug. Suitable effective amounts may be between about 0.01 percent by weight (wt %) and about 20 wt % of the composition, such as between 0.1 wt % and 15 wt %, or between 0.1 wt % and 10 wt % of the composition.

3. Absorption Enhancers

Exemplary absorption enhancers include surfactants, fatty acids and bile acid salts, bile acids, medium chain glycerides, steroidal detergents, acyl carnitine and alkanoylcholines, N-acetylated α-amino acids and N-acetylated non-α-amino acids, calcium chelators, protein kinase C activators, cytochalasins B or D, and medium chain alkylglycosides including dodecylmaltoside and tetradecylmaltoside.

Suitable bile acids include taurocholic acid, glycocholic acid (derivatives of cholic acid), taurochenodeoxycholic acid, glycochenodeoxycholic acid (derivatives of chenodeoxycholic acid), deoxycholic acid, lithocholic acid, and their salts. Salts can be formed with alkali metals, such as sodium and potassium. An exemplary absorption enhancer may be sodium or potassium glycocholate.

The absorption enhancers are typically present in the polymer matrix in an amount effective to enhance sustained release of the drug. Suitable effective amounts may be between about 0.01 percent by weight (wt %) and about 20 wt % of the composition, such as between 0.1 wt % and 15 wt %, or between 0.1 wt % and 10 wt % of the composition.

4. Drugs to be Delivered

Drugs to be delivered may be therapeutic, prophylactic, diagnostic or neutraceutical drugs. The drugs may be small molecules, nucleic acids, proteins, and vaccines.

a. Small Molecules

Exemplary small molecule compounds include anti-cancer agents, for example alkylating agents (such as cisplatin, carboplatin, oxaliplatin, mechlorethamine, cyclophosphamide, chlorambucil, dacarbazine, lomustine, carmustine, procarbazine, chlorambucil and ifosfamide), antimetabolites (such as fluorouracil (5-FU), gemcitabine, methotrexate, cytosine arabinoside, fludarabine, and floxuridine), antimitotics (including taxanes such as paclitaxel and decetaxel, epothilones A-F, and vinca alkaloids such as vincristine, vinblastine, vinorelbine, and vindesine), anthracyclines (including doxorubicin, daunorubicin, valrubicin, idarubicin, and epirubicin, as well as actinomycins such as actinomycin D), cytotoxic antibiotics (including mitomycin, plicamycin, and bleomycin), topoisomerase inhibitors (including camptothecins such as camptothecin, irinotecan, and topotecan as well as derivatives of epipodophyllotoxins such as amsacrine, etoposide, etoposide phosphate, and teniposide), and combinations thereof.

Exemplary small molecule compounds include antimicrobial agents, such as agents against viral, bacterial or fungal infection. Antimicrobial agents include neomycin, streptomycin, chloramphenicol, cephalosporin, ampicillin, penicillin, tetracycline, and ciprofloxacin griseofulvin, ketoconazole, itraconizole, amphotericin B, nystatin, and candicidin, antihistamines/antipruritics (e.g., hydroxyzine, diphenhydramine, chlorpheniramine, brompheniramine maleate, cyproheptadine hydrochloride, terfenadine, clemastine fumarate, triprolidine, carbinoxamine, diphenylpyraline, phenindamine, azatadine, tripelennamine, dexchlorpheniramine maleate, and methdilazine); antibacterial agents (e.g., amikacin sulfate, aztreonam, chloramphenicol, chloramphenicol palmitate, ciprofloxacin, clindamycin, clindamycin palmitate, clindamycin phosphate, metronidazole, metronidazole hydrochloride, gentamicin sulfate, lincomycin hydrochloride, tobramycin sulfate, vancomycin hydrochloride, polymyxin B sulfate, colistimethate sodium, and colistin sulfate); antiviral agents (e.g., interferon alpha, beta or gamma, zidovudine, amantadine hydrochloride, ribavirin, and acyclovir); antimicrobials (e.g., cephalosporins such as cefazolin sodium, cephradine, cefaclor, cephapirin sodium, ceftizoxime sodium, cefoperazone sodium, cefotetan disodium, cefuroxime e azotil, cefotaxime sodium, cefadroxil monohydrate, cephalexin, cephalothin sodium, cephalexin hydrochloride monohydrate, cefamandole nafate, cefoxitin sodium, cefonicid sodium, ceforanide, ceftriaxone sodium, ceftazidime, cefadroxil, cephradine, and cefuroxime sodium; penicillins such as ampicillin, amoxicillin, penicillin G benzathine, cyclacillin, ampicillin sodium, penicillin G potassium, penicillin V potassium, piperacillin sodium, oxacillin sodium, bacampicillin hydrochloride, cloxacillin sodium, ticarcillin disodium, azlocillin sodium, carbenicillin indanyl sodium, penicillin G procaine, methicillin sodium, and nafcillin sodium; erythromycins such as erythromycin ethylsuccinate, erythromycin, erythromycin estolate, erythromycin lactobionate, erythromycin stearate, and erythromycin ethylsuccinate; and tetracyclines such as tetracycline hydrochloride, doxycycline hyclate, and minocycline hydrochloride, azithromycin, clarithromycin); hormone analogues (e.g., androgens such as danazol, testosterone cypionate, fluoxymesterone, ethyltestosterone, testosterone enathate, methyltestosterone, fluoxymesterone, and testosterone cypionate; estrogens such as estradiol, estropipate, and conjugated estrogens; progestins such as methoxyprogesterone acetate, and norethindrone acetate; corticosteroids such as triamcinolone, betamethasone, betamethasone sodium phosphate, dexamethasone, dexamethasone sodium phosphate, dexamethasone acetate, prednisone, methylprednisolone acetate suspension, triamcinolone acetonide, methylprednisolone, prednisolone sodium phosphate, methylprednisolone sodium succinate, hydrocortisone sodium succinate, triamcinolone hexacetonide, hydrocortisone, hydrocortisone cypionate, prednisolone, fludrocortisone acetate, paramethasone acetate, prednisolone tebutate, prednisolone acetate, prednisolone sodium phosphate, and hydrocortisone sodium succinate; or thyroid hormones such as levothyroxine sodium), or a combination of two or more of these agents.

b. Nucleic Acids

Synthetic and natural nucleic acids including RNA, DNA, anti-sense RNA, triplex DNA, inhibitory RNA (RNAi), aptamers, and oligonucleotides, synthetic and natural nucleic acids including RNA, DNA, anti-sense RNA, triplex DNA, inhibitory RNA (RNAi), aptamers, and oligonucleotides). Nucleic acids are more typically listed in terms of base pairs or bases (collectively "bp"). Nucleic acids with lengths above about 10 bp may be used. More typically, useful lengths of nucleic acids for probing or therapeutic use will be in the range from about 20 bp (probes; inhibitory RNAs, etc.) to tens of thousands of bp for genes and vectors. The active agents may also be hydrophilic molecules, and in some embodiments, have a low molecular weight.

Exemplary proteins may be peptides, glycoproteins, hormones, cytokines, and enzymes. For example, proteins may include insulin, insulin derivatives, heparin, albumin, growth hormones, glucagon-like peptide-1 analogues, calcitonin, human granulocyte colony stimulating factors, octreotide, macrotonin, and combinations thereof.

c. Proteins

The drugs to be delivered include synthetic and natural proteins (including enzymes, peptide-hormones, receptors, growth factors, antibodies, signaling molecules), and biologically active portions thereof. Suitable proteins have a size greater than about 1,000 Da for small peptides and polypeptides, more typically at least about 5,000 Da and often 10,000 Da or more for proteins. Suitable antibodies and antibody fragments may include polypeptides and proteins between 10,000 Da and 150,000 Da, as well as larger polypeptides.

Insulin

Generally, insulin refers to human or non-human, recombinant, purified or synthetic insulin or insulin analogues, unless otherwise specified. The insulin in the composition may be recombinant insulin, such as human recombinant insulin produced by recombinant DNA technology, or synthetic insulin analogue, such as insulin glargine, or a combination thereof.

Current insulin formulations include various formulations for injection or inhalation.

Rapid-acting insulin is a type of insulin that starts to lower blood glucose within 5 to 10 minutes after injection and has its strongest effect 30 minutes to 3 hours after injection, depending on the type used. It usually begins to work about 15 minutes after injection, peaks in about 1 hour, and continues to work for 2 to 4 hours. These include Insulin glulisine (APIDRA®, Aventis Pharma S.A.), insulin lispro (HUMALOG®, Eli Lilly and Company), and insulin aspart (NOVOLOG®, Novo Nordisk)

Regular or Short-acting insulin is a type of insulin that starts to lower blood glucose within 30 minutes after injection and has its strongest effect 2 to 5 hours after injection. It usually reaches the bloodstream within 30 minutes after injection, peaks anywhere from 2 to 3 hours after injection, and is effective for approximately 3 to 6 hours. These include human recombinant insulin (HUMULIN® R, Eli Lilly and Company, and NOVOLIN® R, Novo Nordisk).

Intermediate-acting insulin is a type of insulin that starts to lower blood glucose within 1 to 2 hours after injection and has its strongest effect 6 to 12 hours after injection, depending on the type used, examples include lente insulin and NPH insulin. It generally reaches the bloodstream about 2 to 4 hours after injection, peaks 4 to 12 hours later, and is effective for about 12 to 18 hours. These include human recombinant insulin NPH (HUMULIN® N, Eli Lilly and Company, NOVOLIN® N, Novo Nordisk).

Long-acting insulin is a type of insulin that starts to lower blood glucose within 4 to 6 hours after injection and has its strongest effect 10 to 18 hours after injection. It generally reaches the bloodstream several hours after injection and tends to lower glucose levels fairly evenly over a 24-hour period. These include insulin detemir (LEVEMIR®, Novo Nordisk) and insulin glargine (LANTUS®, Sanofi-Aventis).

Inhaled insulin begins working within 12 to 15 minutes, peaks by 30 minutes, and is cleared from the subject in 180 minutes. These include inhaled insulin in Technosphere insulin-inhalation system (AFREZZA®, MannKind Corporation).

Vaccine Antigens

Exemplary vaccines include inactivated vaccines, subunit vaccines, toxoid vaccines, DNA vaccines, recombinant vaccine, or combinations thereof.

The vaccines typically include antigenic materials, such as an infectious agent or cellular antigen, to be delivered to antigen presenting cells to induce immunological responses in a patient in need thereof. Exemplary antigens include infectious disease antigens, killed or attenuated infectious agents such antigens from hepatitis, influenza, and polio, and protozoans such as *Plasmodium* (malaria) and *Leishmania*. Other antigens are antigenic proteins or haptens such as carbohydrate or sugar antigens effective as antigens for these infectious agents, as cancer antigens, or as immunostimulants.

Cellular antigens include tumor antigens, abnormal cellular proteins, and mammalian cellular components produced by viral, bacterial, or protozoan infected cells.

d. Imaging Agents

The drugs may include an imaging label to trace the distribution of the drug, or to detect the accumulation of the drug at a particular site. Drugs with imaging labels may be used for diagnostic drugs used for non-invasive imaging of the subject. Exemplary imaging labels and drugs with imaging labels include radionuclide-labeled small molecules, such as Technetium99 ($^{99m}$Tc), F-18 fluorodeoxyglucose, fluorinated compounds, such as fluorinated silicon oil, perfluorocarbon, or perfluoropolyether containing $^{19}$F, superparamagnetic iron oxide (SPIO), gadolinium, europium, diethylene triamine pentacetic acid (DTPA), 1,4,7,10-tetraazacyclododecane-1,4,7,10-tetraacetic acid (DOTA) and their derivatives, gas, and fluorescent tracers. Suitable modalities with respective tracers are known in the art (Baum et al., *Theranostics*, 2(5)437-447 (2012)).

5. Effective Amount

Typically, the drug to be delivered is included in the polymeric matrix in an amount releasing an effective amount of the drug for at least at least two days, at least four days, at least five days, at least six days, at least seven days, or at least eight days, following single administration to the subject. Suitable amounts include between 5 wt % and 50 wt % of the polymeric matrix, or between 1 wt % and 50 wt % of the formulation.

For example, the amount of the drug to be delivered may be incorporated between about 5 wt % and 45 wt %, 5 wt % and 40 wt %, 5 wt % and 35 wt %, 5 wt % and 30 wt %, 5 wt % and 25 wt %, 5 wt % and 20 wt %, 5 wt % and 15 wt %, or 5 wt % and 10 wt % of the composition.

For example, the amount of the drug to be delivered may be incorporated between about 1 wt % and 45 wt %, 1 wt % and 40 wt %, 1 wt % and 35 wt %, 1 wt % and 30 wt %, 1 wt % and 25 wt %, 1 wt % and 20 wt %, 1 wt % and 15 wt %, or 1 wt % and 10 wt % of the formulation.

B. Drug Delivery Formulations

1. Excipients

The formulation may include one or more one or more physiologically acceptable excipients. Formulation of drugs is discussed in, for example, Hoover, John E., Remington's Pharmaceutical Sciences, Mack Publishing Co., Easton, Pa. (1975), and Liberman, H. A. and Lachman, L., Eds., Pharmaceutical Dosage Forms, Marcel Decker, New York, N.Y. (1980).

The compositions may be combined with one or more excipients to promote rapid dissolution in gastric or intestinal media. Suitable excipients include wetting agents such as polysorbates, glycerin and poloxamers, non-ionic and ionic surfactants, food acids and bases (e.g. sodium bicarbonate), and alcohols, and buffer salts for pH control.

Stabilizers are used to inhibit or retard drug decomposition reactions which include, by way of example, oxidative reactions. A number of stabilizers may be used. Suitable stabilizers include simple alcohols, such as glycerol (or glycerin, or glycerine); bacteriostatic agents such as phenol, benzyl alcohol, meta-cresol (m-cresol) and methylparaben; isotonic agents, such as sodium chloride, glycerol (or glycerin, or glycerine), and glucose; lecithins, such as example natural lecithins (e.g. egg yolk lecithin or soya bean lecithin) and synthetic or semisynthetic lecithins (e.g. dimyristoylphosphatidylcholine, dipalmitoylphosphatidylcholine or distearoyl-phosphatidylcholine; phosphatidic acids; phosphatidylethanolamines; phosphatidylserines such as distearoyl-phosphatidylserine, dipalmitoylphosphatidylserine and diarachidoylphospahtidylserine; phosphatidylglycerols; phosphatidylinositols; cardiolipins; and sphingomyelins).

2. Enteric Coatings and Capsules

The formulation may include an enteric coating, and/or be enclosed in a capsule.

The composition is typically coated with, inserted into, and/or otherwise applied to a coating or a carrier to form a dosage formulation containing an effective amount of one or more drugs. The coating may be inert materials and excipients. The coatings may be added to the composition separately or independently. Different shapes of the composition may be are available and may be dependent on the application.

Exemplary coatings include, for example, enteric coating polymers (e.g. EUDRAGIT® (Evonik Roehm Gmbh Limited Liability Company), hydroxypropyl methylcellulose derivatives, hypromellose, etc.) that form films, layers or capsules, suppository bases (e.g. glycerin, gelatin, glycerinated gelatin, etc.).

a. Enteric Coatings

The compositions may be coated with an enteric coating for release of the drug-polymer matrix at intestinal pH. Suitable pH values for release of the polymeric matrix from the formulation are pH over 5.5, such as between 5.5 and 8.

Exemplary enteric coatings include anionic polymers with methacrylic acid as a functional group (EUDRAGIT®, Evonik Roehm Gmbh Limited Liability Company), such as EUDRAGIT® L30, EUDRAGIT® L100, EUDRAGIT® S100, and combinations thereof. The combinations may be any desired ratio to provide release of the polymeric matrix at pH between 5.5 and 8. Suitable ratios may be 1:1, 1:2, 1:3, 1:4, and 1:5.

b. Capsules

The compositions may be included in a capsule, such as in a hard-shelled or soft-shelled capsule.

Hard-shelled capsules include gelatin and contain dry, powdered ingredients or miniature pellets. These are made in two halves: a lower-diameter "body" that is filled and then sealed using a higher-diameter "cap".

Soft-shelled capsules use oils and the drug is dissolved or suspended in the oil.

Both of these classes of capsules are made from aqueous solutions of gelling agents, such as animal protein (mainly gelatin) or plant polysaccharides or their derivatives (such as carrageenans and modified forms of starch and cellulose). Other ingredients can be added to the gelling agent solution including plasticizers such as glycerin or sorbitol to decrease the capsule's hardness, coloring agents, preservatives, disintegrants, lubricants and surface treatment.

C. Drug Delivery Platforms with Controlled Onset and Duration of Drug Bioactivity Typically, modifications to the composition of the delivery platform may be used to control the onset and duration of the drug action. For example, the use of one polymer instead of a mixture of several polymers may result in a rapid effect for a shorter duration of action. For example, the use of one polymer instead of a mixture of several polymers may reduce the duration of drug action from three days to one day. In addition, smaller pieces of the layered matrices result in a rapid effect and shorter duration of action as compared to larger pieces. For example, smaller pieces may reduce the duration of action from one day to few hours. The shape of the matrices varies, and can be of any shape, such as ovoid, rectangle, triangle, square, circle, etc., and be a large piece with a surface area between 2 $cm^2$ and 7 $cm^2$, of and small piece with a surface area between about 0.1 $cm^2$ and 1 $cm^2$.

Oral administration provides longer duration of action (for several days) due to the gastrointestinal pH (neutral to basic), whereas vaginal administration results in a faster dissolution of the polymer matrix and hence faster onset and shorter duration of action due to the acidic vaginal environment. For example, vaginal administration may provide an onset of drug action within a time period between 30 min and 4 hours following administration, and last for a time period between about 4 and 24 hours.

The type of drug (e.g. unmodified vs. chemically modified drug) also influences the onset and duration of action.

II. Methods of Making the Drug Delivery Compositions and Formulations

Generally, the method of making the compositions includes entrapping one or more drugs to be delivered in a polymeric matrix, in the presence of protease inhibitors, and/or absorption enhancers, and then freeze-drying the matrices.

The compositions may be prepared by mixing at least two different polymers, at a suitable ratio, such as between 1:1 and 1:8 weight ratio, followed by the addition of the drug. The mixture is then stirred for about one hour, during which a suitable concentration of one or more protease inhibitors and/or absorption enhancers is added. Suitable concentrations for the protease inhibitors and/or absorption enhancers are between 0.01 wt % and 20 wt %. After stirring, the mixture is freeze-dried into a matrix. The freeze-dried matrix may be in a form of sandwich of crosslinked layers with the drug entrapped within the matrix, between the layers, or both within the matrix and between the layers. The matrix is then folded and used to form dosage forms.

Typically, the sandwich is formed spontaneously upon mixing the polymers at the appropriate weight ratio in water, and then freeze-drying the polymer mix. After the polymers are combined in water at a suitable concentration, such as at a concentration between 0.5% and 10% for each of the polymers, a suitable crosslinker may be added at between 0.05 wt % and 5 wt % of the composition. Mixing of the polymers forms a crosslinked or network matrix, which, when freeze-dried, forms a layered matrix. The two sandwich layers in the matrix may be crosslinked to each other, or the polymers within the sandwich layers may be crosslinked to each other, or both the polymers within the sandwich layers, and between the sandwich layers may be crosslinked to each other.

Generally, the method of making the formulations includes combining the compositions with excipients, and/or coatings to form formulations suitable for oral, vaginal or rectal administration. The formulations may be in solution form, in gel form, or in a form or a tablet, capsule, pellet, strip, or suppository.

A. Polymers and Polymeric Fibers

The compositions may include one or more drugs in a crosslinked polymeric matrix, or entrapped between two or more polymeric layers. The matrix may be formed from unmodified polymers interconnected by non-covalent intermolecular interactions, crosslinked polymers, polymeric nanofibers, and combinations thereof.

1. Crosslinked Polymers

The crosslinking of the polymers may be achieved by any suitable crosslinking method. Crosslinking may be via light, such as UV light (photopolymerization), electron beam crosslinking, thermo-crosslinking, chemical crosslinking with an initiator, or non-covalent crosslinking though non-covalent interactions.

Suitable initiators and activators for chemical crosslinking are known in the art. These include, but are not limited to, free radical initiators, atom transfer radical polymerization (ATRP) initiators, nitroxide mediated polymerization (NMP) initiators, ionic polymerization initiators, amine photochemical coinitiators, and organic photoinitiators.

Two classes of initiators are peroxide and azo compounds. Radicals may be generated by thermal or ambient redox conditions. Decomposition rates for some initiators vary with pH and the presence of amines.

Exemplary crosslinking agents include sodium tripolyphosphate, ammonium persulfate, hydroxymethanesulfinic acid monosodium salt, potassium persulfate, and sodium persulfate.

2. Electrospun Polymers

The polymers may be in a form of nanofibers. Typically, nanofibers may be generated from polymer solutions using electrospinning.

Methods of electrospinning polymers are known in the art (Agarwal et al., *Polymer*, 49:5603-5621 (2008); Pham et al., *Tissue Engineering*, 12(5):1197-1211 (2006); Padmakumar et al., *ACS Appl. Mater. Interfaces*, 8(11):6925-6934 (2016); and US Patent Application Publication No. US 2016/0367722).

In an exemplary method, chitosan nanofibers may be prepared as follows. Chitosan salt (acetate) solutions at different concentrations may be prepared by dissolving chitosan powder of different molecular weights and acetylation degrees in acetic acid of varying strengths. Chitosan can be obtained from commercial suppliers with different molecular weights and degree of acylation.

The solution is heated at 50° C. for 2 h under continuous stirring, and the stirring continues overnight at room temperature. After electrospinning, chitosan nanofibers are dried under vacuum overnight to remove acetic acid and water residues. The chitosan nanofibers are stored in a desiccator until characterization. Transmission electron microscopy may be utilized to measure the average dimensions of the formed nanofibers.

Factors useful to obtain fibers on the nanoscale include molecular weight of chitosan, concentrations of the chitosan and acetic acid solutions, homogeneity and viscosity of chitosan solution, applied electric field, beading rate, the distance between collector and needle of the electrospinning instrument.

Suitable conditions to obtain chitosan nanofibers may be medium and high molecular weight chitosan, such as between 190,000 Da and 375,000 Da chitosan, between 1% and 10% chitosan dissolved in acetic acid solution at a strength between 3% and 10% acetic acid, applied voltage of about 25 kV, flow rate about 0.4 mL/h, the distance between needle tip and the collector of between 5 cm and 20 cm.

B. Making a Drug-Polymer Matrix

The drug is dissolved in the polymer mix at a concentration of between 5% and 50% of the total weight of the composition, and stirred for one hour. Inclusion of protease inhibitors and/or absorption enhancers into the drug-polymer mixture enhances bioactivity of the drug in the composition when delivered orally, vaginally, or rectally. The mixture is then freeze-dried and the lyophilized mixtures are compressed into tablets and/or coated with enteric-coating polymer, such as anionic polymers with methacrylic acid as a functional group (EUDRAGIT®, Evonik Roehm Gmbh Limited Liability Company), such as EUDRAGIT®L30, L100 or 5100, or combination of them), or may be filled into acid-resistant capsules, or mixed with suppository bases (e.g. glycerinated gelatin) for rectal and vaginal applications.

Additional agents added to the composition or to the formulation include components which may enhance or keep unchanged the bioactivity of the first drug in the composition. Exemplary additional agents include agents that provide additional or different biological activity or physicochemical stability (e.g., sugars, such as, mannitol, sucrose, trehalose, oral hypoglycemic agents, GLP-1, zinc chloride, glycerol, metacresol, sodium hydroxide, hydrochloric acid, and the like).

1. Exemplary Method Forming a Protein-Polymer Matrix

In an exemplary method, any one of cellulose, oxidized regenerated cellulose, dextran, pectin, alginate, or chitosan may be mixed with any one of cellulose, oxidized regenerated cellulose, dextran, pectin, alginate, or chitosan so that the mix is formed from at least two different polymers. The two different polymers are mixed at a weight ratio of 1:1, 1:2, 1:3, 1:4, or 1:5. For example, when the mix includes chitosan and pectin, these polymers are mixed at a weight ratio of 1:1.

A drug to be delivered, such as a hormone, a protein, or a polypeptide, is added to the polymer mix at about 10-30 wt %. For example, the drug insulin is added at about 15 wt % of the composition to the polymer mix. A protease inhibitor, e.g., aprotinin, and an absorption enhancer, e.g., sodium glycocholate, may be added to the mix at a combined concentration of about 0.5 wt %, 1 wt %, 1.5 wt %, or 2 wt %. For example, aprotinin and sodium glycocholate may be added at about 1 wt %, each added at 0.5 wt % to the formulation.

The mixture is then stirred for one hour and freeze-dried into a drug-polymer matrix. The freeze-dried matrix is in a form of sandwich of crosslinked layers with insulin entrapped within the matrix or between the layers. The matrix may then be folded and filled into acid resistant capsules.

C. Cutting into Shape and Folding

The freeze-dried (lyophilized) drug-polymer matrix may be cut into any suitable size. The cutting can be achieved by any suitable means, such as by manual cutting the drug-polymer matrix, or by using an automated form-cutting apparatus.

The drug-polymer matrix is cut to a size suitable for folding into a shape suitable for used for oral, vaginal, or rectal delivery. Suitable sizes may be between 0.1 mm and 50 mm (5 cm) for length, and between 0.1 mm and 50 mm (5 cm) for width, such as between 0.5 mm and 40 mm, 1 mm and 30 mm, 5 mm and 25 mm, 5 mm and 20 mm, 5 mm and 10 mm, or 1 mm and 5 mm for length, and between 0.5 mm and 40 mm, 1 mm and 30 mm, 5 mm and 25 mm, 5 mm and 20 mm, 5 mm and 10 mm, or 1 mm and 5 mm for width.

Once cut to a suitable size, the drug-polymer matrix may be folded into a three-dimensional shape. Suitable three-dimensional shapes include cylinders, square, cuboids, ovoid, sphere, and others.

D. Coating

Once folded, the drug-polymer matrixes are coated with an enteric coating, mixed with excipients and enclosed in a capsule, or both.

E. Storage and Stability

The various formulations may be stored at the room temperature or be refrigerated. When stored at ambient room temperature for over three months, the formulations and compositions provide drug delivery to the subjects, demonstrating no need for refrigeration.

Compositions and formulations may be stored at ambient room temperature or refrigerated for up to 3 months, up to six months, up to a year, without substantial loss in performance. Substantial loss in performance indicates a loss of about 10% or less in bioactivity of the drug when compared to the bioactivity of the same drug at the same concentration in freshly prepared composition or formulation.

III. Methods of Using the Drug Delivery Compositions

Drug delivery compositions provide prolonged delivery of an effective amount of the drug after a single administration to a subject.

A. Dosage Regime

The formulations may be provided in doses delivering an effective amount of the one or more drugs. The effective amount typically includes an amount of a drug effective to alleviate, reduce, ameliorate one or more symptoms of a disease of condition over an period of time after a single administration. In some diseases or conditions, a single dose may be sufficient to change the level of the target molecule by about 20% or more following single administration. Typically, the administration is via oral, vaginal, or rectal routes.

The effective amount of the drug may be released from the formulation over a period of two days, three days, four days, five days, six days, seven days, or eight days. The drug may remain bioactive in vivo over a period of two days, three days, four days, five days, six days, seven days, or eight days. A second or subsequent dose may be administered to the same subject biweekly, once every four days, once weekly, or less frequently. The formulations may be administered for as long as is necessary to treat a disease or disorder.

The effective amount of the drug delivered to a subject after a single administration is typically safe, well-tolerated, and does not cause severe adverse reactions. For example, the formulation may deliver an effective amount of insulin to a subject with diabetes without causing hypoglycemia (lower than normal blood glucose level in the subject) during the period of action of the drug.

The amount of the drug to be delivered may be between about 5 wt % and 45 wt %, 5 wt % and 40 wt %, 5 wt % and 35 wt %, 5 wt % and 30 wt %, 5 wt % and 25 wt %, 5 wt % and 20 wt %, 5 wt % and 15 wt %, or 5 wt % and 10 wt % of the composition.

The amount of the drug to be delivered may be between about 1 wt % and 45 wt %, 1 wt % and 40 wt %, 1 wt % and 35 wt %, 1 wt % and 30 wt %, 1 wt % and 25 wt %, 1 wt % and 20 wt %, 1 wt % and 15 wt %, or 1 wt % and 10 wt % of the formulation.

The amount of the drug to be delivered may also be presented as international units (IU) of the drug, or international units of the drug per kg of body weight (IU/kg). A single dosage unit may be formulated to deliver between 0.01 IU/kg and 100 IU/kg of drug.

A single dosage unit may be formulated to deliver between 0.001 mg/kg and 100 mg/kg of the drug following single administration.

B. Mucoadhesion

After reaching the gastrointestinal tract, and the dissolution of the coating layers (if present), the folded matrices of the drug delivery compositions mix with the gastrointestinal fluids and swell. Upon swelling, the drug-polymer matrices, such as sandwich-like drug-polymer matrixes with the drug entrapped inside, unfold and at least a part of the drug-polymer matrix adheres to the gastrointestinal wall. From this position, the matrices release the drug over several days.

Similar to the compositions administered orally, the compositions administered vaginally or rectally undergo release and unfolding of the drug-polymer matrices after administration. At least a part of each drug-polymer matrix adheres to the vaginal or rectal wall. The drug-polymer matrices then release the drug over a period between one and eight days.

C. Subjects to be Treated

Typically, the subjects to be treated include humans, other mammals and animals suffering from a disease or condition. The subjects may be adults, children, or domestic pets.

The drug delivery compositions offer the advantage of sustained delivery of the entrapped drugs from the gastrointestinal tract, which reduces the frequency of administration and the cost, and improves patient compliance. It may also reduce adverse reactions associated with the repeated administration of the carriers and their entrapped cargoes.

The drug delivery compositions may be beneficial to subjects and care providers by lowering the frequency of administration.

D. Diseases to be Treated

The compositions may be used to alleviate, reduce, or ameliorate one or more symptoms of a disease in a subject.

Diseases to be treated include hormonal deficiency, enzymatic deficiency, overactive immune system, autoimmune diseases, and proliferative diseases.

Exemplary diseases or conditions to be treated include pre-diabetes, Type I diabetes, Type II diabetes, gestational diabetes, Type I juvenile diabetes, Maturity Onset Diabetes of the Young (MODY) diabetes, LADA (latent autoimmune diabetes in adults), bacterial, viral, or parasitic infections, autoimmune diseases such as systemic lupus erythematosus, inflammatory bowel disease, Crohn's disease, allergies, such as food allergies, and proliferative diseases, such as oral cancers, cancers of the gastrointestinal tract, and others.

All Type II diabetic patients (including pregnant women, pre- and post-operative) may be treated with the drug delivery formulations alone or in combination with all other forms of oral anti-diabetic drugs that work via other mechanisms of actions.

The subjects with the diseases to be treated may be suffering from further complication, including renal failure or heart diseases, liver cirrhosis or end stage liver diseases, dementia, weight loss, patients with Type II diabetes who are thin patients and in need to regain their weights and cannot use metformin as a first line of therapy, Type II diabetic patients with indication to shift from oral anti-diabetic drugs to insulin therapy as in pregnancy, diabetic foot and surgical operations, patients with eye complications, stroke, dementia, who cannot use insulin injections.

E. Combination Therapies

The drug delivery compositions may be administered alone or in combination with additional treatments, or additional active agents, such as second active agent. The second active agent may be used to increase or decrease the level of the same target molecule as the first active agent, or of a different target molecule, within the same subject.

In some embodiments, the second active agent is a known agent for treating hormonal deficiency, enzymatic deficiency, overactive immune system, autoimmune diseases, or proliferative diseases. In some embodiments, the second active agent is one that modulates the effect of the first drug delivered with the drug delivery compositions. In some embodiments, the second active agent increases the efficacy, enhances the effect, or otherwise improves the performance or the first drug.

F. Advantages of the Drug Delivery Compositions

The drug delivery compositions and formulations are typically stable at room temperature for over 3 months, such as for four months, five months, or six months. The compositions and formulations do not require special storage instructions, and have reduced cost by eliminating the need for special storage and transportation conditions.

When the disclosed acting composition carrying insulin was used to treat Type I or Type II diabetes, the observed reduction in fasting blood glucose level was better as compared with conventional insulin injection, or relative to a placebo (no treatment).

The compositions and formulations may improve patient compliance by including a combination of drugs and thereby reducing frequency of administration. For example, a composition or formulation containing insulin as the drug to be delivered, may also contain various forms of insulin and glucagon-like peptide 1 receptor agonists (GLP-1). GLP-1 or others formulated with insulin into the same delivery system.

The compositions and formulations are suitable for oral, vaginal, or rectal administration, and therefore are simple to administer. The compositions and formulations are well tolerated. When used to treat Type I or Type II diabetes, the formulations produced no hypoglycemia even at high doses, no epigastric pain, vomiting, abdominal pain, diarrhea, or nausea, and influenced fasting and postprandial blood glucose levels.

IV. Kits

Kits containing the compositions are also provided.

In some aspects, the kit contains a pre-mixed combined composition, which contains a therapeutic, prophylactic, diagnostic, or neutraceutical agent in a polymer matrix and a pharmacologically acceptable excipient. The compositions and the formulations may be in sterile form. The combined compositions may be provided in the form of a liquid, gel, capsule, tablet, pellet, suppositories, cream, or spray. The compositions may be available in a kit ready for use form.

Instructions for use of the kit are also typically provided.

The present disclosure will be further understood by reference to the following non-limiting examples.

EXAMPLES

Diabetes Overview

Glucose is a simple sugar used by all the cells of the body to produce energy and support life. Humans need a minimum level of glucose in their blood at all times to stay alive. The primary manner in which the body produces blood glucose is through the digestion of food. When a person does not get glucose from food digestion, glucose is produced from stores in the tissue and released by the liver. The body's glucose levels are regulated by insulin. Insulin is a peptide hormone that is naturally secreted by the pancreas. Insulin helps glucose enter the body's cells to provide a vital source of energy.

When a healthy individual begins a meal, the pancreas releases a natural spike of insulin called the first-phase insulin release. In addition to providing sufficient insulin to process the glucose coming into the blood from digestion of the meal, the first-phase insulin release acts as a signal to the liver to stop making glucose while digestion of the meal is taking place. Because the liver is not producing glucose and there is sufficient additional insulin to process the glucose from digestion, the blood glucose levels of healthy individuals remain relatively constant and their blood glucose levels do not become too high.

Diabetes is a disease characterized by abnormally high levels of blood glucose and inadequate levels of insulin. There are two major types of diabetes—Type 1 and Type 2. In Type 1 diabetes, the body produces no insulin. In the early stages of Type 2 diabetes, although the pancreas does produce insulin, either the body does not produce the insulin at the right time or the body's cells ignore the insulin, a condition known as insulin resistance.

Even before any other symptoms are present, one of the first effects of Type 2 diabetes is the loss of the meal-induced first-phase insulin release. In the absence of the first-phase insulin release, the liver will not receive its signal to stop making glucose. As a result, the liver will continue to produce glucose at a time when the body begins to produce new glucose through the digestion of the meal. As a result, after eating, the blood glucose level of patients with diabetes goes too high, a condition known as hyperglycemia. Hyperglycemia causes glucose to attach unnaturally to certain proteins in the blood, interfering with the proteins' ability to perform their normal function of maintaining the integrity of the small blood vessels. With hyperglycemia occurring after each meal, the tiny blood vessels eventually break down and leak. The long-term adverse effects of hyperglycemia include blindness, loss of kidney function, nerve damage and loss of sensation and poor circulation in the periphery, potentially requiring amputation of the extremities.

Between two and three hours after a meal, an untreated diabetic's blood glucose becomes so elevated that the pancreas receives a signal to secrete an inordinately large amount of insulin. In a patient with early Type 2 diabetes, the pancreas can still respond and secretes this large amount of insulin. However, this occurs at the time when digestion is almost complete and blood glucose levels should begin to fall. This inordinately large amount of insulin has two detrimental effects. It puts an undue extreme demand on an already compromised pancreas, which may lead to its more rapid deterioration and eventually render the pancreas unable to produce insulin, and too much insulin after digestion leads to weight gain, which may further exacerbate the disease condition.

Current Treatments for Diabetes and their Limitations

Because patients with Type 1 diabetes produce no insulin, the primary treatment for Type 1 diabetes is daily intensive insulin therapy. The treatment of Type 2 diabetes typically starts with management of diet and exercise. Although helpful in the short-run, treatment through diet and exercise alone is not an effective long-term solution for the vast majority of patients with Type 2 diabetes. When diet and exercise are no longer sufficient, treatment commences with various non-insulin oral medications. These oral medications act by increasing the amount of insulin produced by the pancreas, by increasing the sensitivity of insulin-sensitive cells, by reducing the glucose output of the liver or by some combination of these mechanisms. These treatments are limited in their ability to manage the disease effectively and generally have significant side effects, such as weight gain and hypertension. Because of the limitations of non-insulin treatments, many patients with Type 2 diabetes deteriorate over time and eventually require insulin therapy to support their metabolism. As their insulin resistance progresses, higher and higher doses of insulin are required to lower glucose levels. Concentrated insulin up to U-500 (500 units per ml) is commercially available for these patients, but it is limited to basal use due to a slow absorption profile.

Insulin therapy has been used for more than 80 years to treat diabetes. This therapy usually involves administering several injections of insulin each day. These injections consist of administering a long-acting basal injection one or two times per day and an injection of a fast-acting insulin at meal-time. Although this treatment regimen is accepted as effective, it has limitations. Patients generally dislike injecting themselves with insulin due to the inconvenience and pain of needles. As a result, patients tend not to comply adequately with the prescribed treatment regimens and are often improperly medicated.

Even when properly administered, insulin injections do not replicate the natural time-action profile of insulin. In particular, the natural spike of the first-phase insulin release in a person without diabetes results in blood insulin levels rising within several minutes of the entry into the blood of glucose from a meal. By contrast, injected insulin enters the blood slowly, with peak insulin levels occurring within 80 to 100 minutes following the injection of regular human insulin.

A potential solution is the injection of insulin directly into the vein of diabetic patients immediately before eating a meal. In studies of intravenous injections of insulin, patients exhibited better control of their blood glucose for 3 to 6 hours following the meal. However, for a variety of medical reasons, intravenous injection of insulin before each meal is not a practical therapy.

One of the key improvements in insulin treatments was the introduction in the 1990s of rapid-acting insulin analogs, such as HUMALOG® (insulin lispro), NOVOLOG® (insulin aspart) and APIDRA® (insulin glulisine). However, even with the rapid-acting insulin analogs, peak insulin levels typically occur within 50 to 70 minutes following the injection. Because the rapid-acting insulin analogs do not adequately mimic the first-phase insulin release, diabetics using insulin therapy continue to have inadequate levels of insulin present at the initiation of a meal and too much insulin present between meals. This lag in insulin delivery can result in hyperglycemia early after meal onset. The excessive insulin between meals may result in an abnormally low level of blood glucose known as hypoglycemia. Hypoglycemia can result in loss of mental acuity, confusion, increased heart rate, hunger, sweating and faintness. At very low glucose levels, hypoglycemia can result in loss of consciousness, coma and even death. According to the American Diabetes Association, or ADA, insulin-using diabetic patients have on average 1.2 serious hypoglycemic events per year, many of which events require hospital emergency room visits by the patients.

The following examples demonstrate the efficacy of the drug delivery formulations for the oral administration of insulin in animal models and to humans.

Examples describe the use of formulations containing proteins (e.g. insulin) incorporated into a crosslinked matrix between two or more different polysaccharides, such as dextran, pectin, alginate, or chitosan. In some embodiments where chitosan is used, the chitosan is in the form of nanofibers and crosslinked using sodium tripolyphosphate. Insulin, in percentages of 5-50% of the total weight, was dissolved in the mixed polysaccharide matrix and stirred for one hour. Drug-polymer matrices may be prepared at any desired weight, such as between 0.5 gram and 100 gram, or more.

Inclusion of protease inhibitors and/or absorption enhancers into the insulin and polysaccharide mixture plays a crucial rule in enhancing the oral bioactivity and hypoglycemic effect of the oral delivery systems. The mixture was then freeze-dried and the lyophilized mixtures were compressed into tablets and coated with enteric-coating polymer, for example, EUDRAGIT® (Evonik Roehm Gmbh Limited Liability Company, such as EUDRAGIT® L30, L100 or S100, or combination of them). Alternatively the mixture can be filled into acid-resistant capsules, or mixed with a suppository base (e.g. glycerinated gelatin) for rectal and vaginal applications.

The various formulations were then stored at the room temperature and were tested in animals or humans after 3 months, in some cases, to test whether they can maintain the insulin hypoglycemic activities after storage at ambient room temperature, without the need for refrigeration. The same formulations were used in both the animal studies and the pilot clinical trials.

Example 1. Oral Insulin Improves and Prolongs In Vivo Hypoglycemic Effect in Rabbits and Goats Materials and Methods
Formulations The formulations were prepared by first preparing a drug-polymer matrix of a desired weight. Chitosan and pectin were mixed in water, at 1:1 weight ratio, to form a 1% polysaccharide solution. The polymers in the solution were not crosslinked and were not in nanofiber form. The crosslinking between the hydroxyl groups of pectin and the amino groups of chitosan to form the crosslinked- or network-like structures or layers occurred during stirring. This was followed by the addition of human recombinant insulin at about 15 wt % of the composition. Aprotinin and sodium glycocholate, to about 1 wt % for both, each at about 0.5 wt % of the composition, were also added during the stirring of chitosan and pectin. The mixture was then stirred for one hour and freeze-dried. The freeze-dried matrix was in a form of a sandwich of crosslinked layers with insulin entrapped within the matrix, between the layers, and both within the matrix and between the layers.

The final composition of the drug-polymer matrix contained about 42 wt % chitosan, about 42 wt % pectin, about 15 wt % of the drug insulin, about 0.5 wt % aprotinin, and 0.5 wt % sodium glycocholate.

The matrix was then folded and filled into enteric acid resistant capsules.

Administering to a Subject

Adult rabbits and goats (males and females) were purchased locally. Rabbits were kept in large cages, and both rabbits and goats allowed food and water ad libitum. Animals were divided randomly into different groups (n=3). Diabetes was induced in animals by single intraperitoneal injection of streptozotocin (65 mg/Kg) or alloxan (150 mg/Kg). Groups received the commercial injectable insulin (subcutaneously) or the insulin delivery systems of varying compositions (orally via the use of stomach feeding tubes or vaginally). The protocol was approved by the Assiut University Ethical Committee. Blood glucose was monitored by using the CONTOUR® PLUS blood glucose monitoring system (Bayer Pharmaceuticals Pvt. Ltd., Berlin, Germany) and the CONTOUR® PLUS test strips (Bayer Pharmaceuticals Pvt. Ltd., Berlin, Germany). Serum insulin was measured in a Diagnostic Laboratory using ARCHITECT i1000SR immunoassay analyzer (Abbott Diagnostics, Lake Forest, Ill.).

To ensure that the results could be repeated in larger animal models, and whether the effect would be sustained over several days, the formulations were tested in diabetic goats. Diabetes was induced in goats using the same method utilized in the rabbits after ACTRAPID® (2 IU/Kg, Novo Nordisk, Bagsvaerd, Denmark) was injected subcutaneously into the goat to test whether the resulting hypoglycemic effect is similar to what has been reported in literature in animals and in human.

Results

The formulation formed according to the above method contained two layers of polymeric matrices. Each layer was a mix of chitosan and pectin, where insulin and the other ingredients are entrapped between the two layers or within the layers.

The formulation showed improved results, as compared to the commercial injectable insulin, with exceptionally longer duration. In all the experiments, animals were allowed water and food.

The first experiment was a preliminary experiment in a diabetic rabbit model with a high dose (100 IU/Kg) to test the efficacy of the insulin delivery system (FIG. 1). A strong hypoglycemic effect was observed in the rabbit, which lasted over almost three days. No signs of inflammation were observed when the pathology of the intestinal mucosa was examined.

Figure 2A:
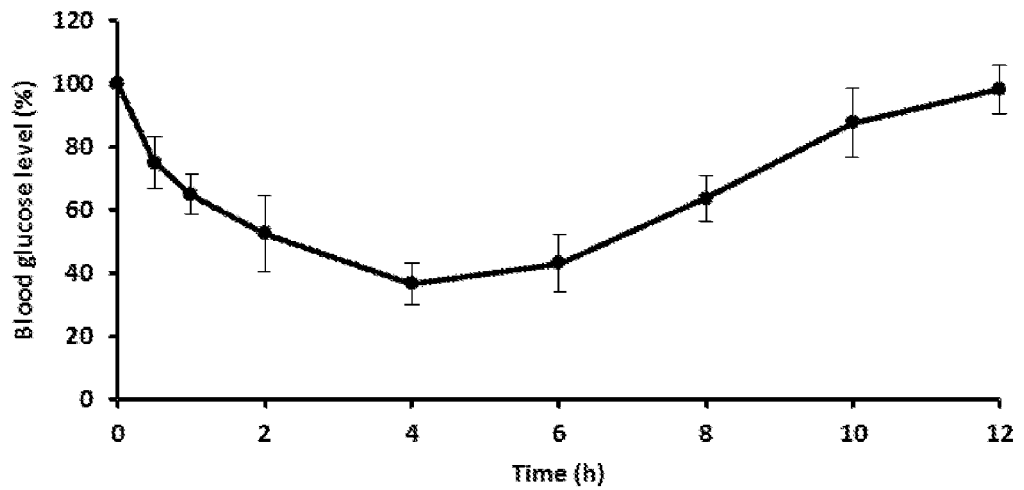
FIG. 2A is a line graph showing the blood glucose level (as percentage of the initial level) over time (h) in a diabetic goat following subcutaneous administration of ACTRAPID® (clear colorless solution containing 100% neutral human insulin) (2 IU/Kg).
Figure 2B:
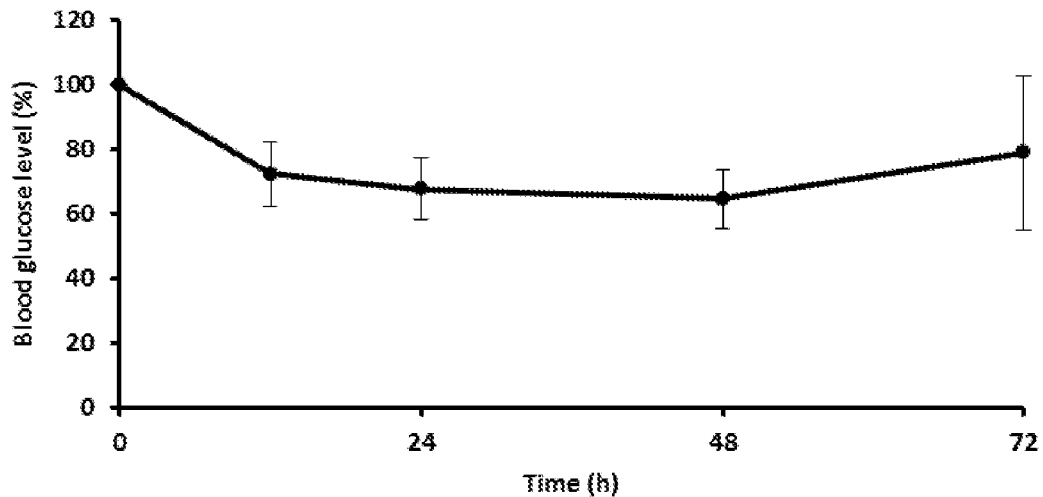
FIG. 2B is a line graph showing the blood glucose level (as percentage of the initial level) over time (h) in a diabetic goat following oral administration of the insulin delivery system (10 IU/Kg).
Figure 3A:
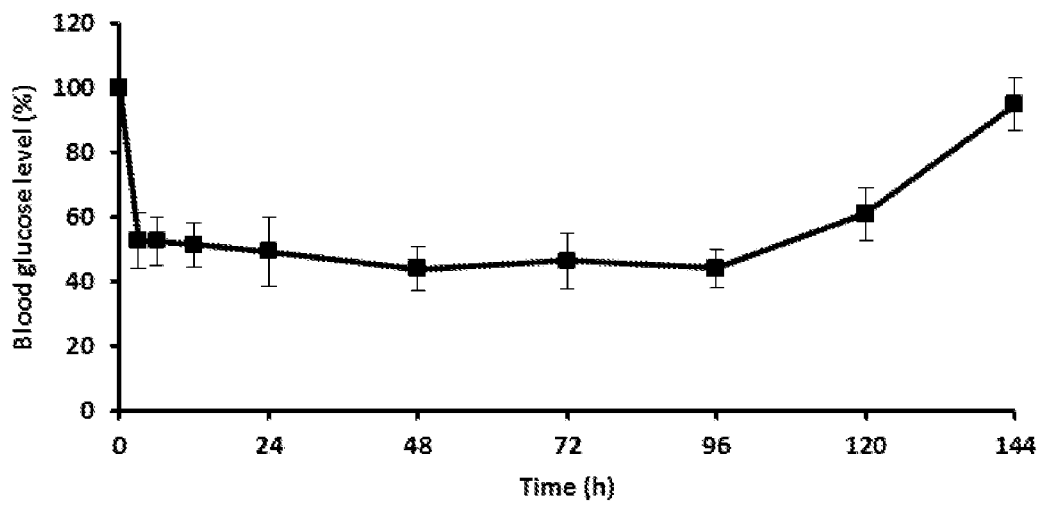
FIGS. 3A and 3B are line graphs showing the blood glucose level (as percentage of the initial level) (FIG. 3A) and serum insulin levels (uU/ml) (FIG. 3B) over time (h) in a diabetic goat following oral administration of the insulin delivery system (50 IU/Kg).
Figure 3B:
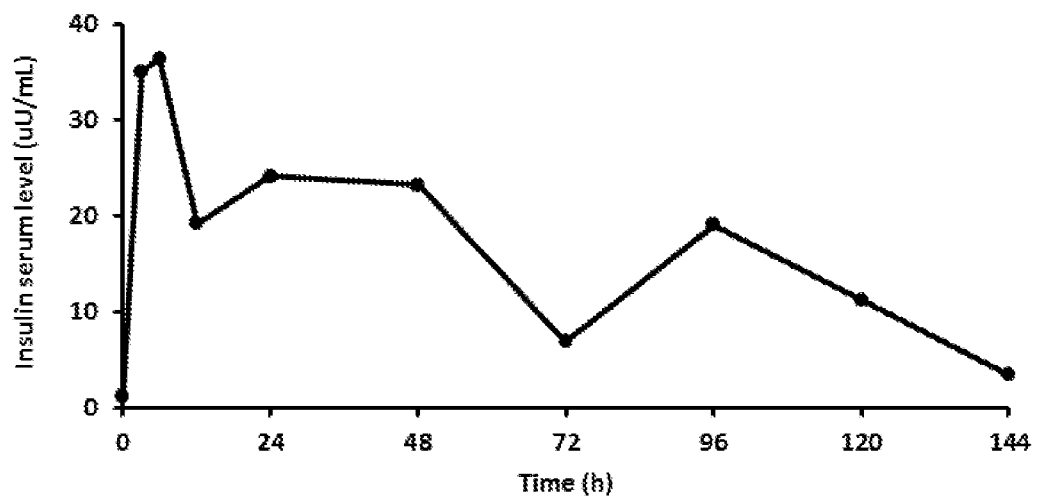

Studies in the goats showed a hypoglycemic effect over about twelve hours was observed after injecting the rapidly acting insulin, which is similar to the duration of action of this type of insulin in animals and in humans (FIG. 2A). Hence, diabetic goat was useful as a model of diabetes with partially similar responsiveness as in human. When a small dose of 10 IU/Kg of the insulin delivery system was orally administered to the goat, a sustained hypoglycemic effect was observed over 72 h, which is quite similar to the hypoglycemic effect observed in the rabbit (FIG. 2B). However, the hypoglycemic effect was not as strong as in the rabbits, which might be explained by the lower dose of insulin (10 IU/Kg in the goats vs. 100 IU/Kg in the rabbits). When a larger dose of 50 IU/Kg of the insulin delivery system was administered orally to the goat, a sustained and stronger hypoglycemic effect was observed over 144 h (i.e. 6 days) (FIGS. 3A and 3B). Hence, duration and potency of the delivery system could be controlled by altering the dose of the loaded insulin. No severe hypoglycemia was observed at high doses in rabbits or in goats.

All data together indicate that this insulin delivery system is able to control the release of their entrapped cargoes and release them over time, and protect them from enzymatic and proteolytic degradation in the gastrointestinal tract.

Example 2: Vaginal Administration of Insulin Formulation

The insulin delivery system of Example 1 was modified for vaginal applications.

Figure 4:
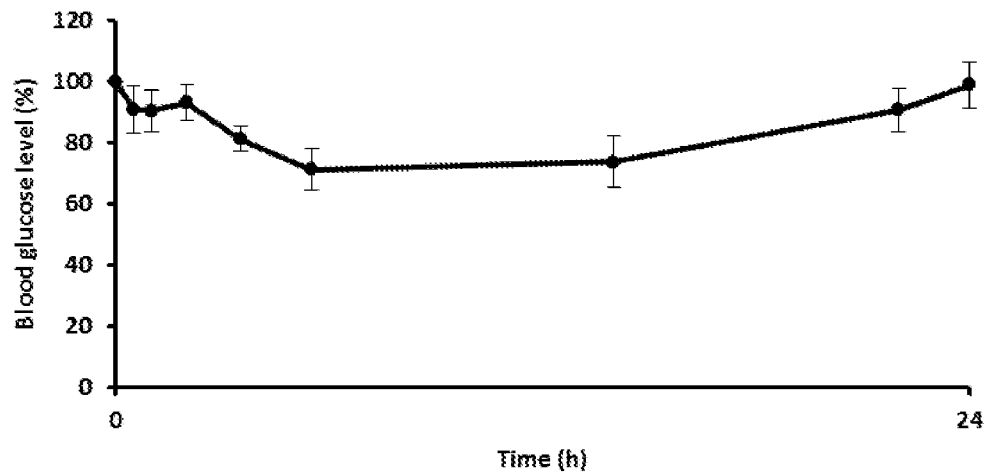
FIG. 4 is a line graph showing the blood glucose level (as percentage of the initial level) over time (h) in a diabetic goat following vaginal administration of the insulin delivery system (50 IU/Kg).
Figure 5:
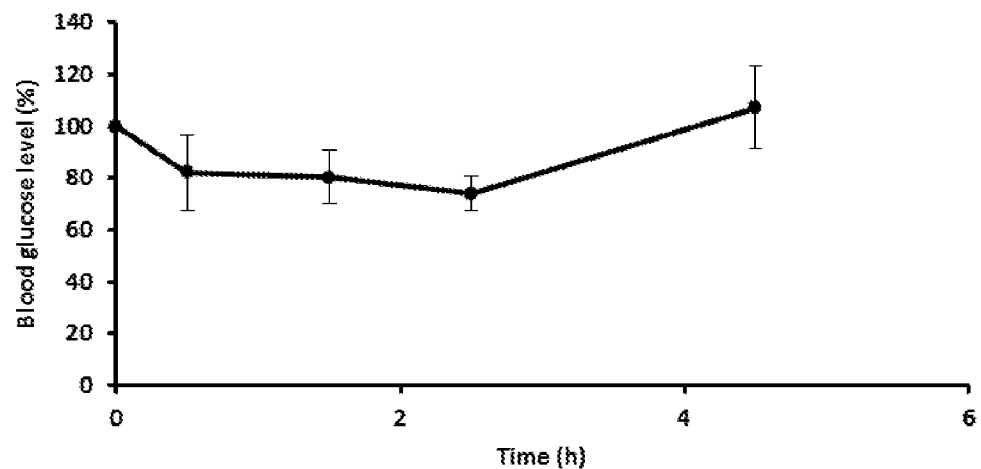
FIG. 5 is a line graph showing the blood glucose level (as percentage of the initial level) over time (h) in a diabetic goat following vaginal administration of the insulin delivery system prepared using a modified preparation method (50 IU/Kg). In this formulation, the matrix was not folded but was cut into small pieces to accelerate the release and diffusion of insulin from the matrix, and thus faster onset and shorter duration of action were observed.

The rate of drug release and duration of action could be controlled over 24 h or even faster over 5 h, although the same dose (i.e. 50 IU/Kg) was administered vaginally. See FIGS. 4 and 5.

Example 3: Oral Insulin Improves and Prolongs In Vivo Hypoglycemic Effect in Humans Materials and Methods The protocol was approved by the "Ethical Committee" of Assiut University Faculty of Medicine. Informed consents were obtained from all the included subjects. The subjects were human patients. Blood glucose was monitored either by using CONTOUR® PLUS blood glucose monitoring system (Bayer Pharmaceuticals Pvt. Ltd., Berlin, Germany) and the CONTOUR® PLUS test strips (Bayer Pharmaceuticals Pvt. Ltd., Berlin, Germany) or in a Diagnostic Laboratory. Serum insulin was measured in a Diagnostic Laboratory using ARCHITECT i1000SR immunoassay analyzer (Abbott Diagnostics). Blood glucose and hemoglobin A1c were measured in a Diagnostic Laboratory using ARCHITECT c4000 clinical chemistry analyzer (Abbott Diagnostics).

Based on the promising results of the experimental trials, a protocol for clinical assessment was established to assess the use of the formulation on human subjects for controlling of blood glucose level. The main goals were to evaluate the safety and efficacy of the delivery platform. Clinical assessment slightly varied from a case-to-case, due to ethical considerations and clinical circumstances. However, for comparison, all external factors and treatment strategies in both animal and human experiments were fixed, except for the type of insulin delivery, which was either injectable insulin or oral administration of insulin loaded into the insulin delivery system.

The insulin delivery system was tested in a "proof-of-concept" pilot clinical study on six (males and females) chronic uncontrolled (hemoglobin A1c: ca. 8.8-11.3%), Type I and Type II diabetic patients (variable duration of the disease: 4 months-12 years), with body weight of 50-118 kg, age of 19-62 years old, with different complications of diabetes and with other co-morbid diseases.

Results

The hypoglycemic effect after single oral administration was stronger than the effect observed after injection of insulin. Moreover, the effect could be, remarkably, sustained for about four days with some modifications of the oral formulation. In addition, the insulin system was able to return the postprandial blood glucose level to the baseline within few hours. The insulin delivery system was also safe and well-tolerated, and no hypoglycemia (blood glucose level<normal level) was observed even at high doses.

Those patients were mostly complicated by one or more of other chronic diseases, such as, hypertension, peripheral neuropathy, chronic hepatitis C virus, retinopathy, fatty liver and frozen shoulder, and most of them are on combinational therapy. One patient was Type I diabetes, whereas the other five patients were Type II diabetes. All of the patients were resistant to the treatment, and they were on regimen of multiple hypoglycemic drugs that work via different mechanisms (i.e. insulin therapy (intermediate acting) and oral hypoglycemic drugs).

Significant differences as compared to the injectable insulin were observed. No complications related to the use of the oral delivery systems were recorded. Additionally, all the patients were under follow up after the experiments with no reported complications.

Figure 6:
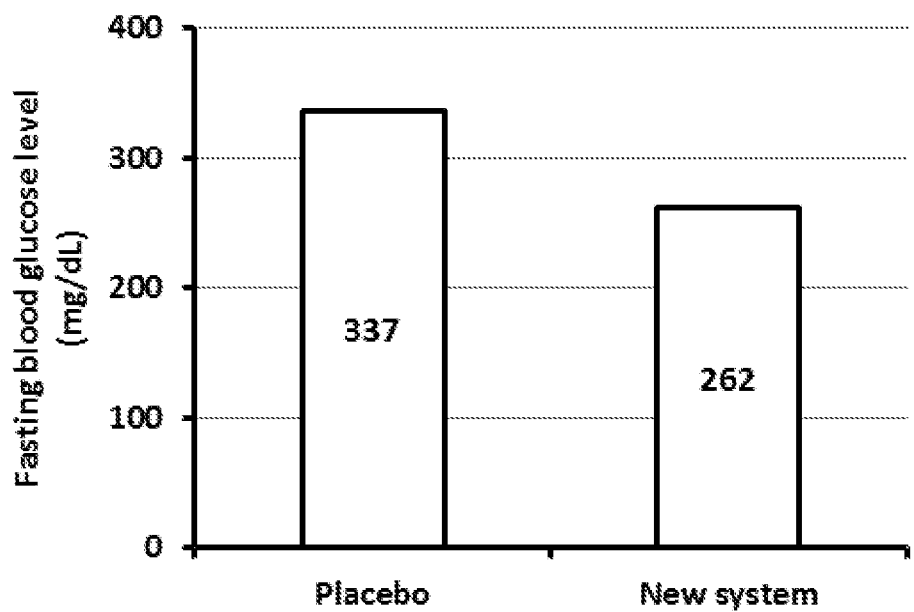
FIG. 6 is a bar graph showing the fasting blood glucose concentrations (mg/dL) in a first human diabetic patient following oral administration of the insulin delivery system (9.4 IU/Kg) or placebo (no treatment).

The first case was a female (weight 80 Kg, 55 years old) with Type II diabetes. She has compensated liver cirrhosis with normal liver functions and mild hypertension. She also has peripheral neuropathy and gall bladder stones and chronic hepatitis C virus. She was diagnosed as diabetic since 11 years (HgA1c=10.8). She was controlled on oral AMARYL® tablets (Glimepiride, Sanofi-Aventis) (3 mg tablets, twice a day, morning and evening), and insulin injection (intermediate acting, MIXTARD at 40 IU, one dose in the morning). With insulin alone, she had a blood sugar level>350, which indicate that she is partially responding to insulin. Hence, AMARYL® tablets (Glimepiride, Sanofi-Aventis) was added to her regimen. She received a single oral dose of 9.4 IU/Kg of the insulin with the insulin delivery system. Surprisingly, the blood sugar level was reduced to 262 vs. 337 for the placebo (i.e. no treatment), although she has not received the AMARYL® tablets (Glimepiride, Sanofi-Aventis) during the treatment period of the oral insulin (FIG. 6).

Figure 7A:
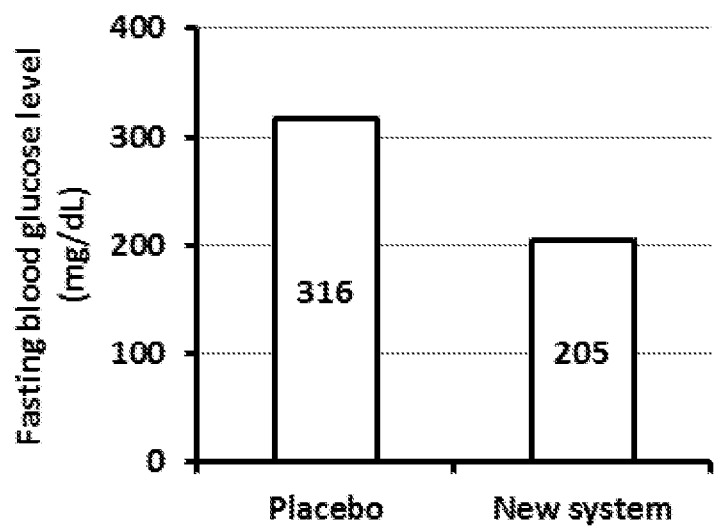
FIGS. 7A and 7B are bar graphs showing the fasting blood glucose concentrations (mg/dL, FIG. 7A) and serum insulin levels (uU/mL, FIG. 7B) in the second human diabetic patient following oral administration of the insulin delivery system (13.6 IU/Kg) or placebo.
Figure 7B:
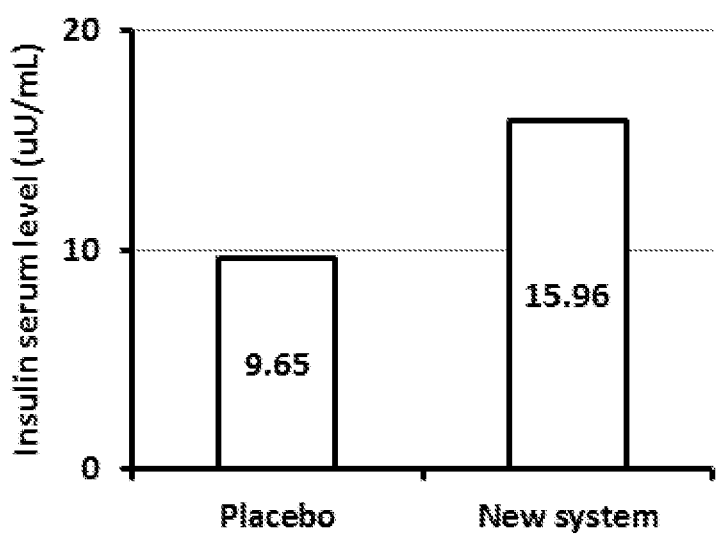

The second case was a female (weight 118 Kg, 55 years old) with Type II diabetes. She was diagnosed as diabetic since 9 years (HgA1c=9.7). She was controlled on oral AMARYL® Tablets (Glimepiride, Sanofi-Aventis) (3 mg tablets, twice a day, morning and evening), and insulin injection (Mixtard at 60 IU, one dose in the morning). She had hypertension, peripheral neuropathy, eye affection, fatty liver and chronic hepatitis C virus. She received a single oral dose of 13.6 IU/Kg of the insulin in the insulin delivery system. The blood sugar level was reduced to 205 vs. 316 for the placebo, although she has not received the AMARYL® (Glimepiride, Sanofi-Aventis) tablets during the period of the oral treatment (FIGS. 7A and 7B). Interestingly, the serum insulin level was also increased from 9.65 in the case of placebo to 15.96 after receiving the oral insulin with the insulin delivery system. The placebo was no treatment, and insulin or glucose levels reflect insulin or glucose levels before the treatment.

Figure 8A:
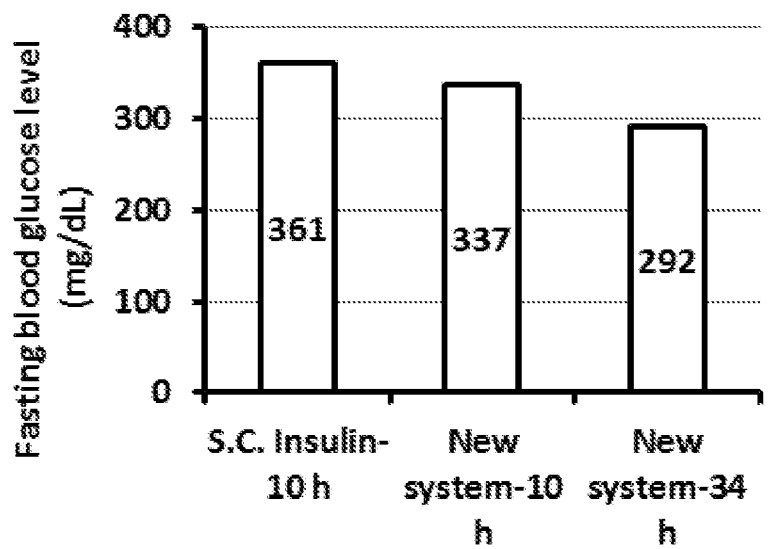
FIGS. 8A and 8B are bar graphs showing the fasting blood glucose concentrations (mg/dL, FIG. 8A) and serum insulin level (uU/mL, FIG. 8B) in the third human diabetic patient following oral administration of the insulin delivery system (32 IU/Kg) or subcutaneous injection of ACTRAPID® (0.6 IU/Kg).
Figure 8B:
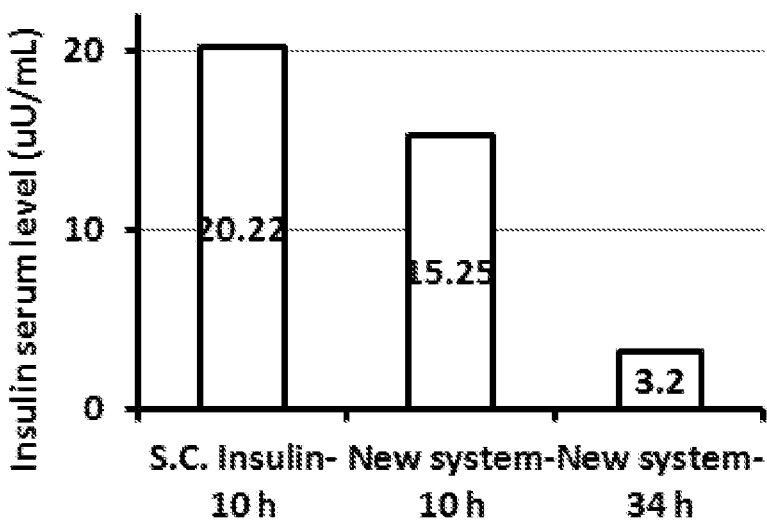

The third case was a female (weight 50 Kg, 19 years old) with Type I diabetes (Anti-insulin antibody is high=14 and the only case with low C-peptide<1 ng/mL during the whole study, even after the subcutaneous injection or the oral administration of insulin). She was diagnosed as diabetic since 4 months (HgA1c=10.5). She was controlled on LANTUS® 26 IU (insulin glargine, Sanofi-Aventis) before bed time and regular crystalline insulin 4 IU before each of the three meals. She had past history of recurrent ketoacidosis. She received a single oral dose of 32 IU/Kg of the insulin with the insulin delivery system. In this case, the effect of the insulin delivery system was compared to the effect of insulin injection, as placebo could not be applied due to high blood glucose level. After injection of 30 IU of ACTRAPID®, the blood glucose level was 361 (serum insulin level=20.22). After single oral administration, the blood glucose level was reduced to 337 (serum insulin level=15.25), and continued to decrease to 292 after 34 h of the single oral dose (serum insulin level=3.2) (FIGS. 8A and 8B).

Figure 9A:
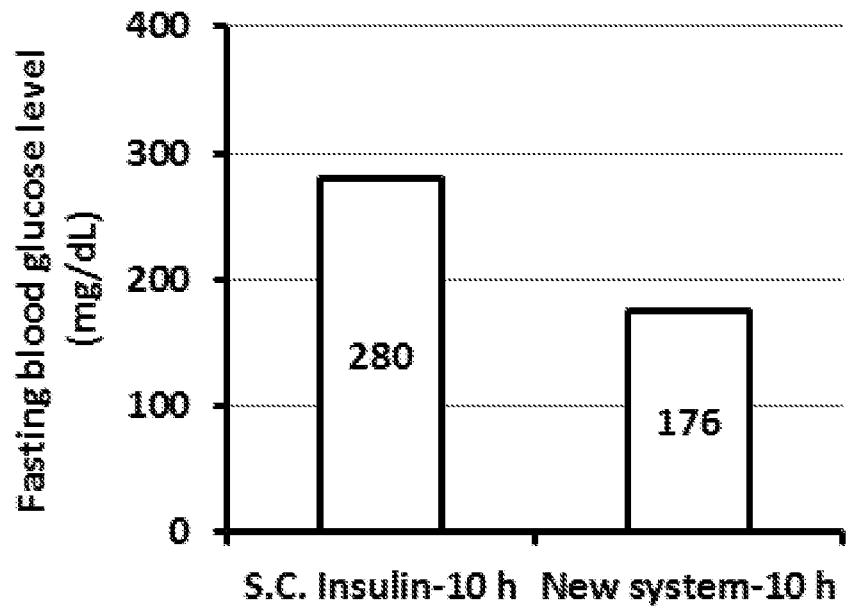
FIGS. 9A and 9B are bar graphs showing the fasting blood glucose concentrations (mg/dL, FIG. 9A) and serum insulin levels (uU/mL, FIG. 9B) in the fourth human diabetic patient following oral administration of the insulin delivery system (17.8 IU/Kg) or subcutaneous injection of ACTRAPID® (0.3 IU/Kg).
Figure 9B:
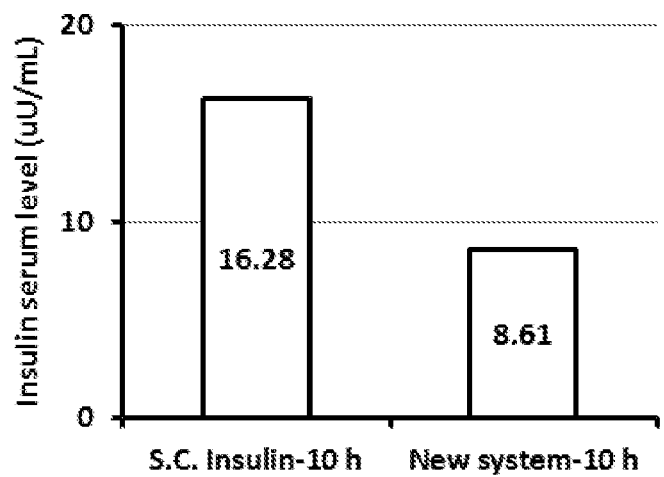

The fourth case was a female (weight 87 Kg, 48 years old) with Type II diabetes. She was diagnosed as diabetic since 3 years (HgA1c=8.8). She was controlled on Mixtard, Metformin and Diamicron 60 mg MR. She has hypertension and fatty liver. She received a single oral dose of 17.8 IU/Kg of the insulin with the insulin delivery system. In this case, the effect of the insulin delivery system was compared to the effect of insulin injection. After injection of 25 IU of ACTRAPID®, the blood glucose level was 280. After single oral administration, the blood glucose level was reduced to 176 (FIGS. 9A and 9B).

Figure 10:
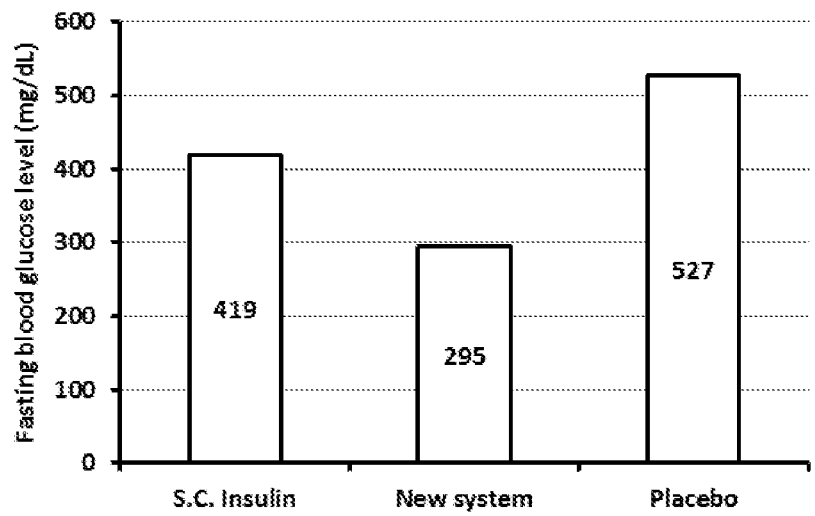
FIG. 10 is a bar graph showing the fasting blood glucose concentrations (mg/dL) in the fifth human diabetic patient following oral administration of the insulin delivery system (25.4 IU/Kg) or subcutaneous injection of ACTRAPID® (0.3 IU/Kg).

The fifth case was a male (weight 59 Kg, 62 years old) with Type II diabetes. He was diagnosed as diabetic since 7 years (HgA1c=11.3). He was controlled on oral hypoglycemic metformin, Diamicron and Glustin. He also has erectile dysfunction, peripheral neuropathy, attacks of hypotension and bronchial asthma. He received a single oral dose of 25.4 IU/Kg of the insulin with the insulin delivery system. In this case, the effect of the insulin delivery system was compared to both the effect of insulin injection and effect of placebo. After injection of 15 IU of ACTRAPID®, the blood glucose level was 419 vs. 527 for the placebo. After single oral administration, the blood glucose level was reduced to 295 (FIG. 10). The placebo was the blood glucose level prior to the injection of ACTRAPID®.

Figure 11A:
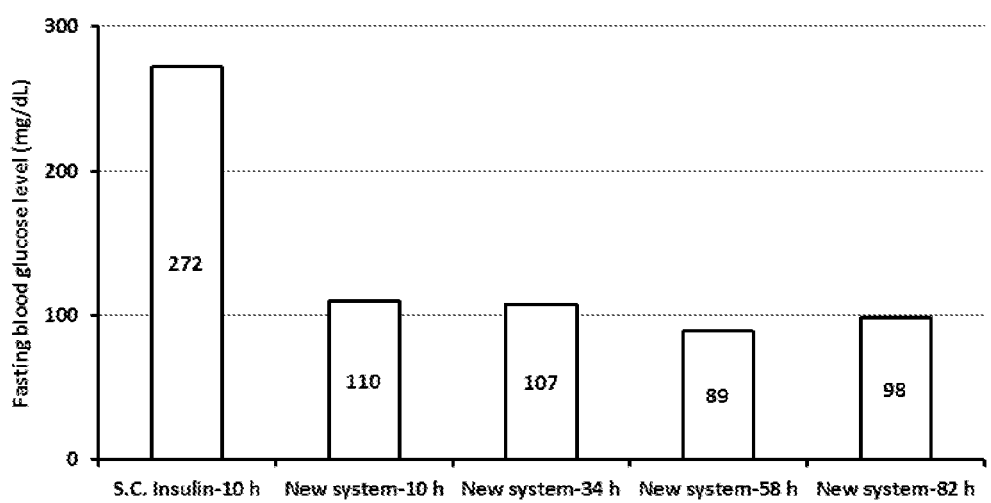
FIGS. 11A and 11B are bar graphs showing the fasting blood glucose concentrations (mg/dL, FIG. 11A) and serum insulin levels (uU/mL, FIG. 11B) in the sixth diabetic patient following single oral administration of the insulin delivery system prepared using insulin glargine instead of unmodified insulin (20 IU/Kg) or subcutaneous injection of LANTUS® (insulin glargine, long active insulin sold by Sanofi-Aventis) (0.2 IU/Kg).
Figure 11B:
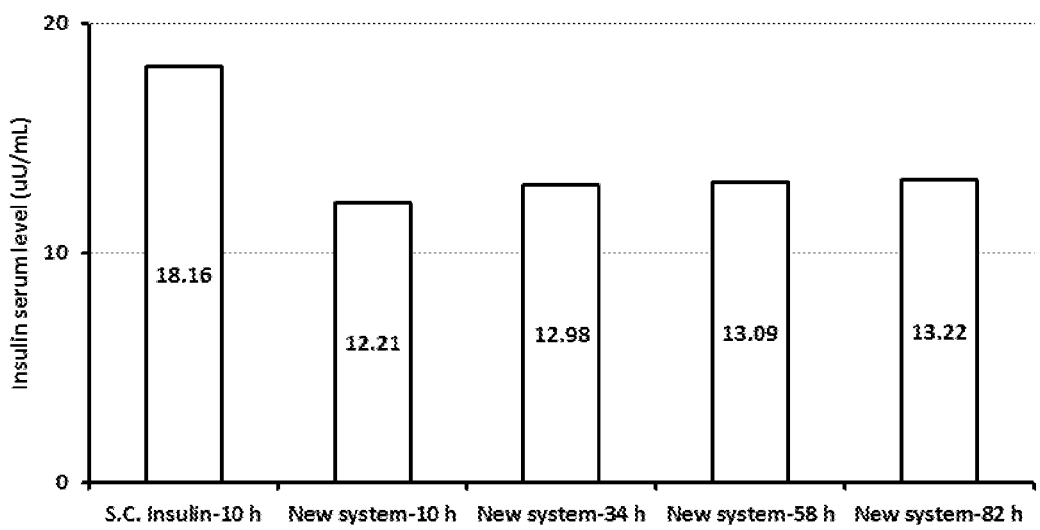

The last and sixth case was a female (weight 96 Kg, 60 years old) with Type II diabetes. She was diagnosed as diabetic since 12 years (HgA1c=8.5). She was controlled on 60 IU Mixtard insulin, cidophage one tablet before breakfast and one tablet before lunch and one tablet Amaryl before dinner. She had hypertension, diabetic foot and ischemic heart diseases. She received a single oral dose of 20 IU/Kg of the insulin with the insulin delivery system, but the preparation method of the insulin delivery system was modified to include insulin glargine instead of unmodified insulin. In this case, the effect of the insulin delivery system was compared to the effect of insulin injection. After injection of 20 IU of insulin, the blood glucose level was 272, 10-h after the subcutaneous administration. After single oral administration, the blood glucose level was reduced to 110, 107, 89, 98, 10-h, 34-h, 58-h, 82-h after the single oral administration, respectively (FIGS. 11A and 11B). Based on the results obtained from this optimized oral delivery system, the single oral dose (20 IU/Kg) might be equivalent to a 5 IU/Kg/day because the 20 IU/Kg single oral dose was effective in maintaining a normal blood glucose levels over 4 days. This dose is considered as a low dose, as compared to the doses reported in literature and in clinical trials.

The data show the diversity of circumstances in which the oral insulin platforms were utilized, e.g., different age, sex, weight and type and severity of diabetes.

The clinical data demonstrate that this technology is an effective tool in controlling different types of diabetes with acceptable efficiency and high safety profile.

The results describe oral dosage forms based on insulin drug delivery technology. The can be adapted for delivery of other drugs, and other routes of administration, with controlling the onset and duration of action. A sustained strong hypoglycemic effect could be attained for several days after administration of a single oral dose to more than one animal model. The hypoglycemic effect was slightly affected by the presence of food. Combined delivery of more than one drug has also been successfully attained. In addition, no special storage or refrigeration was required to preserve the stability of the loaded insulin.

The drug delivery system was tested in a pilot clinical study on six (males and females) chronic uncontrolled (hemoglobin A1c: ca. 8.8-11.3%), Type I and Type II diabetic patients (variable duration of the disease: 4 months-12 years), with body weight of 50-118 kg, age of 19-62 years old, with different complications of diabetes and with other co-morbid diseases. Hypoglycemic effect following single oral administration was stronger than the effect observed after injection of insulin alone. The effect was sustained for about four days. In addition, the described drug delivery system was able to return the postprandial blood glucose level to the baseline within few hours. The insulin delivery system was also safe and well-tolerated, and no hypoglycemia (blood glucose level below normal level) was observed even at high doses.

The following describe some of the embodiments described herein.

1. A drug delivery composition, comprising: a polymer matrix comprising: (1) two or more layers, wherein each layer comprises one or more polymers; (2) an agent comprising: one or more of a therapeutic agent, a prophylactic agent, a diagnostic agent, or a neutraceutical agent, at least a portion of the agent entrapped within the layers of the polymer matrix, between the layers of the polymeric matrix, or entrapped within and between the layers of the polymer matrix; and (3) a protease inhibitor, an absorption enhancer, or a combination thereof, in an amount effective to preserve bioactivity of the agent under conditions present in the gastrointestinal tract; and an enteric coating or capsule encapsulating the polymeric matrix.

2. A pH-responsive delivery composition that at acidic pH forms a capsule-like matrix via a self-sealing process to protect an agent inside, and at neutral pH the pH-responsive delivery composition forms a swollen gel-like matrix that unrolls and adheres to a mucosal surface and release the agent over an extended period of time (e.g., up to one week), the pH-responsive delivery composition, comprising: a polymer matrix comprising: (1) two or more layers, wherein each layer comprises one or more polymers; (2) an agent comprising: one or more of a therapeutic agent, a prophylactic agent, a diagnostic agent, or a neutraceutical agent, at least a portion of the agent entrapped within the layers of the polymer matrix, between the layers of the polymeric matrix, or entrapped within and between the layers of the polymer matrix; and (3) a protease inhibitor, an absorption enhancer, or a combination thereof, in an amount effective to preserve bioactivity of the agent under conditions present in the gastrointestinal tract; and an enteric coating or capsule encapsulating the polymeric matrix.

3. The composition of claim 1 or 2, wherein the one or more polymers are crosslinked.

4. The composition of any of claims 1 to 3, wherein the one or more polymers is a high mechanical strength polymer.

5. The composition of any of claims 1 to 4, wherein the one or more polymers has a pH threshold of 5.5.

6. The composition of any of claims 1 to 5, comprising a mucoadhesive polymer.

7. The composition of any of claims 1 to 6, wherein at least one polymer is a polysaccharide.

8. The composition of claim 6, wherein the polysaccharide is selected from the group consisting of celluloses, dextrans, pectin, alginates, chitosans, and mixtures thereof.

9. The composition of any of claims 1 to 8, wherein the polymers comprise chitosan and pectin.

10. The composition of any of claims 1 to 9, wherein at least one polymer is in the form of a nanofiber or a nanoparticle.

11. The composition of any of claims 1 to 10, wherein the polymer forms a nanofiber or nanoparticle with the agent.

12. The composition of any of claims 1 to 11 comprising two or more polymers, the polymers having a weight ratio of between 1:1 and 1:8.

13. The composition of any of claims 1 to 12, wherein the agent is present at between 5 wt % and 50 wt %, based on the total weight of the composition.

14. The composition of any of claims 1 to 13, wherein the agent is selected from the group consisting of small molecules, proteins, nucleic acids, and vaccines.

15. The composition of any of claims 1 to 14, wherein the agent is selected from the group consisting of proteins, peptides, incretins, and glycoproteins.

16. The composition of any of claims 1 to 15, wherein the agent is selected from the group consisting of hormones, cytokines, chemokines, and enzymes.

17. The composition of any of claims any of claims 1 to 16, wherein the agent is selected from the group consisting of insulin, insulin derivatives, heparin, growth hormones, glucagon-like peptide-1 analogues, calcitonin, human granulocyte colony stimulating factors, octreotide, and macrotonin.

18. The composition of any of claims 1 to 17, wherein the protease inhibitor is aprotinin.

19. The composition of any of claims 1 to 18, wherein the absorption enhancer is glycocholine or sodium caprate.

20. The composition of any of claims 1 to 19, wherein the polymeric matrix is in an enteric coated tablet.

21. The composition of any of claims 1 to 20 formulated for oral, buccal, vaginal, or rectal administration.

22. A method of making the composition of any of claims 1 to 21, comprising: forming a mixture comprising: (i) the agent, (ii) the one or more polymers, and (iii) the protease inhibitor, the absorption enhancer, or a combination thereof and crosslinking the mixture to form a crosslinked matrix comprising layers, nanofibers, nanoparticles, or a combination thereof.

23. The method of claim 22, wherein the mixture further comprises a solvent.

24. The method of claim 22 or 23, wherein crosslinking is performed by mechanical stirring.

25. The method of any of claims 22 to 24, wherein crosslinking is performed by chemical crosslinking.

26. The method of claim 25 wherein the mixture further comprises sodium tripolyphosphate.

27. The method of any of claims 22 to 26 further comprising one or more of freeze drying the crosslinked matrix to form a freeze-dried matrix, solvent evaporating the crosslinked matrixed to form a solvent-evaporated matrix, or lyophilizing the crosslinked matrix to form a lyophilized matrix.

28. The method of any of claims 22 to 26 further comprising encapsulating the crosslinked matrix in an enteric capsule or coating.

29. The method of claim, 27 wherein the freeze-dried matrix is shaped into a desired three-dimensional shape and coated with an enteric coating, by coating or encapsulation into a capsule.

30. A method, comprising: administering to a subject the composition of any one of claims 1 to 21.

31. The method of claim 30, wherein the composition is administered orally, vaginally, or rectally.

32. The method of claim 30 or 31, wherein at least a part of the composition contacts an oral wall, an intestinal wall, a vaginal wall, or a rectal wall of the subject.

33. The method of any of claims 30 to 32, wherein at least a part of the composition adheres to an oral wall, an intestinal wall, a vaginal wall, or a rectal wall of the subject.

34. The method of any of claims 30 to 33, wherein at least a portion of the composition is released at a pH in the range of 5.5 to 7.

35. The method of any of claims 30 to 34, wherein at least a portion of the composition is released at a pH above 7.

36. The method of any of claims 30 to 35, wherein after a single administration, an effective amount of the agent is released from the composition over a period of at least two days, at least three days, at least four days, or at least one week.

37. The method of any of claims 30 to 36, wherein the subject has Type I or Type II diabetes.

38. The method of any of claims 30 to 37, wherein the agent is insulin, and the agent is released over a period of at least one to four days.

39. The method of any of claims 30 to 38, wherein the composition normalizes the subject's blood glucose levels without causing hypoglycemia.

40. The method of any of claims 30 to 39 comprising orally administering to a subject with Type I or Type II diabetes the composition of any one of claims 1 to 19 once daily, once every two days, once every three days, once every four days, or once every seven days.

Unless defined otherwise, all technical and scientific terms used herein have the same meanings as commonly understood by one of skill in the art to which the present disclosure belongs. Publications cited herein and the materials for which they are cited are specifically incorporated by reference.

Those skilled in the art will recognize, or be able to ascertain using no more than routine experimentation, many equivalents to the specific embodiments of the present disclosure described herein. Such equivalents are intended to be encompassed by the following claims. While the foregoing is directed to embodiments of the present disclosure, other and further embodiments of the disclosure may be devised without departing from the basic scope thereof, and the scope thereof is determined by the claims that follow.

We claim:

1. An oral dosage form of a pH-responsive drug delivery composition, comprising:
   a polymer matrix consisting of two layers, the two layers crosslinked to each other, each layer of the two layers comprising crosslinked polymers, the crosslinked polymers derived from chitosan and pectin;
   insulin;
   a protease inhibitor; and
   an absorption enhancer,
   wherein each of the insulin, the protease inhibitor, and the absorption enhancer are entrapped between the two layers of the polymer matrix, within the two layers of the polymer matrix, or entrapped within and between the two layers of the polymer matrix;
   wherein the drug delivery composition protects the insulin at an acidic pH; and
   wherein the drug delivery composition, at neutral pH, forms a swollen matrix that unrolls and adheres to a mucosal surface and releases the insulin over a period of at least 24 hours.

2. An oral dosage form of a pH-responsive drug delivery composition, comprising:
   a polymer matrix consisting of two layers, the two layers crosslinked to each other, each layer of the two layers comprising crosslinked polymers, the crosslinked polymers derived from chitosan and pectin;
   0.1 wt % to 10 wt % of a protease inhibitor based on a total weight of the drug delivery composition;
   0.1 wt % to 10 wt % of an absorption enhancer based on the total weight of the drug delivery composition; and
   5 wt % to 25 wt % insulin based on the total weight of the drug delivery composition,
   wherein each of the insulin, the protease inhibitor, and the absorption enhancer are entrapped between the two layers of the polymer matrix, within the two layers of the polymer matrix, or entrapped within and between the two layers of the polymer matrix;
   wherein the drug delivery composition, at acidic pH, protects the insulin; and
   wherein the drug delivery composition, at neutral pH, forms a swollen matrix that unrolls and adheres to a mucosal surface and releases the insulin over a period of about 24 hours or more.

3. The drug delivery composition of claim 2, wherein the absorption enhancer comprises glycocholic acid, taurochenodeoxycholic acid, glycochenodeoxycholic acid, lithocholic acid, or a salt thereof, or sodium caprate.

4. The drug delivery composition of claim 2, wherein the absorption enhancer is glycocholic acid.

5. The drug delivery composition of claim 2, wherein the absorption enhancer is sodium caprate.

6. The drug delivery composition of claim 2, wherein the protease inhibitor comprises aprotinin, 4-(2-Aminoethyl) benzenesulfonyl fluoride hydrochloride, bestatin hydrochloride, N-(trans-Epoxysuccinyl)-L-leucine 4-guanidinobutylamide, leupeptin, hemisulfate salt, Pepstatin A, or combinations thereof.

7. The drug delivery composition of claim 2, wherein the protease inhibitor is aprotinin.

8. The drug delivery composition of claim 2, wherein the drug delivery composition releases the insulin over a period of 82 hours or more.

9. The drug delivery composition of claim 2, wherein the chitosan and the pectin have a weight ratio of between 1:1 and 1:8.

10. An oral dosage form of a pH-responsive drug delivery composition, comprising:
    a polymer matrix consisting of two layers, the two layers crosslinked to each other, each layer of the two layers comprising crosslinked polymers, the crosslinked polymers derived from chitosan and pectin;
    about 15 wt % insulin based on a total weight of the composition;
    about 1 wt % of a combined amount of aprotinin and glycocholic acid based on the total weight of the composition,
    wherein each of the insulin, the aprotinin, and the glycocholic acid are entrapped between the two layers of the polymer matrix, within the two layers of the polymer matrix, or entrapped within and between the two layers of the polymer matrix;
    wherein the drug delivery composition protects the insulin at an acidic pH; and
    wherein the drug delivery composition, at a neutral pH, forms a swollen matrix that unrolls and adheres to a mucosal surface and releases the insulin over a period of at least 24 hours.

11. The drug delivery composition of claim 1, wherein the protease inhibitor comprises aprotinin, 4-(2-Aminoethyl) benzenesulfonyl fluoride hydrochloride, bestatin hydrochloride, N-(trans-Epoxysuccinyl)-L-leucine 4-guanidinobutylamide, leupeptin, hemisulfate salt, Pepstatin A, or combinations thereof.

12. The drug delivery composition of claim 1, wherein the absorption enhancer comprises taurochenodeoxycholic acid, glycochenodeoxycholic acid, lithocholic acid, glycocholic acid, or a salt thereof, or sodium caprate.

13. The drug delivery composition of claim 1, wherein:
    the protease inhibitor is aprotinin; and
    the absorption enhancer is glycocholic acid.

14. The drug delivery composition of claim 13, wherein:
    a combined amount of the aprotinin and the glycocholic acid in the composition is about 1 wt % based on a total weight of the composition;

an amount of the insulin in the composition is from 5 wt % to 20 wt % based on the total weight of the composition; and a weight ratio of the crosslinked polymers is from 1:1 to 5:1.

* * * * *